US009805163B1

(12) United States Patent
Panch et al.

(10) Patent No.: US 9,805,163 B1
(45) Date of Patent: Oct. 31, 2017

(54) APPARATUS AND METHOD FOR IMPROVING COMPLIANCE WITH A THERAPEUTIC REGIMEN

(71) Applicant: Wellframe, Inc., Boston, MA (US)

(72) Inventors: Trishan Panch, Cambridge, MA (US); Vinayak Ramesh, Boston, MA (US); Archit Bhise, Cambridge, MA (US); Jacob Sattelmair, Cambridge, MA (US)

(73) Assignee: Wellframe, Inc., Boston, MA (US)

( * ) Notice: Subject to any disclaimer, the term of this patent is extended or adjusted under 35 U.S.C. 154(b) by 0 days.

(21) Appl. No.: 14/248,854

(22) Filed: Apr. 9, 2014

Related U.S. Application Data

(63) Continuation of application No. 13/800,973, filed on Mar. 13, 2013.

(51) Int. Cl.
*G06Q 50/00* (2012.01)
*G06F 19/00* (2011.01)

(52) U.S. Cl.
CPC .................................. *G06F 19/325* (2013.01)

(58) Field of Classification Search
CPC ........................................... G06C 50/22–50/24
See application file for complete search history.

(56) References Cited

U.S. PATENT DOCUMENTS

| | | | |
|---|---|---|---|
| 4,803,625 A | 2/1989 | Fu et al. | 364/413.03 |
| 4,889,238 A | 12/1989 | Batchelor | 206/535 |
| 5,233,987 A | 8/1993 | Fabian et al. | 607/41 |
| 5,827,179 A | 10/1998 | Lichter et al. | 600/300 |
| 5,832,448 A | 11/1998 | Brown | 705/2 |
| 6,144,922 A | 11/2000 | Douglas et al. | 702/31 |
| 6,161,095 A | 12/2000 | Brown | 705/2 |
| 6,277,071 B1 | 8/2001 | Hennessy et al. | 600/300 |
| 6,336,900 B1 | 1/2002 | Alleckson et al. | 600/485 |
| 6,385,589 B1 | 5/2002 | Trusheim et al. | 705/2 |
| 6,730,024 B2 | 5/2004 | Freyre et al. | 600/300 |
| 6,870,484 B1 | 3/2005 | Brinsfield et al. | 340/825.49 |
| 6,879,970 B2 | 4/2005 | Shiffman et al. | 706/21 |
| 6,936,007 B2 | 8/2005 | Quy | 600/300 |
| 7,225,013 B2 | 5/2007 | Geva et al. | 600/513 |
| 7,260,480 B1 | 8/2007 | Brown et al. | 702/19 |
| 7,395,216 B2 | 7/2008 | Rosenfeld et al. | 705/2 |
| 7,399,276 B1 | 7/2008 | Brown et al. | 600/300 |
| 7,636,667 B2 | 12/2009 | Brown | 705/2 |

(Continued)

*Primary Examiner* — Jonathan K Ng
(74) *Attorney, Agent, or Firm* — Sunstein Kann Murphy & Timbers LLP

(57) ABSTRACT

A computer-implemented method for improving compliance with a therapeutic regimen for each of a plurality of patients includes, for each patient, causing presentation by the server to the patient via an application running on the mobile computing device, on at least a daily basis, of (i) an updated list of items to be performed by the patient on the date of presentation on the updated list and (ii) a region on a display of the mobile computing device for reporting performance of items on the updated list so as to cause sending by the mobile computing device to the server of patient compliance data; and receiving at the server from the mobile computing device the patient compliance data, storing such data and using such data in calculating the updated list for presentation to the patient via the mobile computing device on a subsequent occasion.

25 Claims, 52 Drawing Sheets

(56) References Cited

U.S. PATENT DOCUMENTS

| | | | |
|---|---|---|---|
| 7,672,884 B2 | 3/2010 | Schuster et al. | 705/35 |
| 7,877,274 B2 | 1/2011 | Brown | 705/3 |
| 7,877,686 B2 | 1/2011 | Abbott et al. | 715/712 |
| 7,983,759 B2 | 7/2011 | Stahmann et al. | 607/60 |
| 8,027,846 B2 | 9/2011 | Schoenberg et al. | 705/2 |
| 8,036,911 B2 | 10/2011 | Bellon et al. | 705/2 |
| 8,170,887 B2 | 5/2012 | Rosenfeld et al. | 705/2 |
| 8,175,895 B2 | 5/2012 | Rosenfeld et al. | 705/3 |
| 8,249,895 B2 | 8/2012 | Faulkner et al. | 705/3 |
| 8,255,238 B2 | 8/2012 | Powell et al. | 705/3 |
| 8,290,788 B2 | 10/2012 | Brown | 705/2 |
| 2002/0032385 A1 | 3/2002 | Raymond et al. | 600/513 |
| 2002/0082865 A1* | 6/2002 | Bianco et al. | 705/2 |
| 2003/0177177 A1 | 9/2003 | Oka et al. | 709/203 |
| 2003/0212579 A1 | 11/2003 | Brown et al. | 705/2 |
| 2004/0054263 A1 | 3/2004 | Moerman et al. | 600/300 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0193446 A1 | 9/2004 | Mayer et al. | 705/2 |
| 2004/0249664 A1 | 12/2004 | Broverman et al. | 705/2 |
| 2005/0187789 A1 | 8/2005 | Hatlestad et al. | 705/2 |
| 2007/0106536 A1 | 5/2007 | Moore | 705/3 |
| 2007/0112602 A1 | 5/2007 | Bellon et al. | 705/3 |
| 2007/0175980 A1 | 8/2007 | Alsafadi | 235/380 |
| 2007/0260482 A1* | 11/2007 | Nurmela et al. | 705/2 |
| 2008/0104615 A1 | 5/2008 | Nolan et al. | 719/328 |
| 2008/0146334 A1 | 6/2008 | Kil | 463/36 |
| 2008/0177576 A1 | 7/2008 | Jennings et al. | 705/3 |
| 2008/0201168 A1* | 8/2008 | Brown | 705/2 |
| 2009/0076338 A1 | 3/2009 | Zdeblick et al. | 600/300 |
| 2009/0093688 A1 | 4/2009 | Mathur | 600/300 |
| 2009/0132580 A1 | 5/2009 | James et al. | 707/102 |
| 2009/0144086 A1 | 6/2009 | Toleti et al. | 705/3 |
| 2009/0253973 A1* | 10/2009 | Bashan et al. | 600/365 |
| 2010/0318424 A1* | 12/2010 | LaValle | 705/14.58 |
| 2011/0010328 A1* | 1/2011 | Patel et al. | 706/52 |
| 2011/0046979 A1 | 2/2011 | Tulipano et al. | 705/2 |
| 2011/0106556 A1* | 5/2011 | Patel et al. | 705/2 |
| 2011/0120470 A1 | 5/2011 | Bowerbank | 128/204.23 |
| 2011/0196702 A1 | 8/2011 | Salouk et al. | 705/3 |
| 2011/0270631 A1* | 11/2011 | Cambray et al. | 705/3 |
| 2012/0123793 A1* | 5/2012 | Werk et al. | 705/2 |
| 2012/0245960 A1 | 9/2012 | Bartholomew, III et al. | 705/3 |
| 2012/0253848 A1 | 10/2012 | Gazula | 705/3 |
| 2012/0259648 A1 | 10/2012 | Mallon et al. | 705/2 |
| 2012/0259652 A1 | 10/2012 | Mallon et al. | 705/2 |
| 2012/0278095 A1 | 11/2012 | Homchowdhury et al. | 705/2 |
| 2012/0278104 A1 | 11/2012 | Traughber et al. | 705/3 |
| 2012/0301864 A1 | 11/2012 | Bagchi et al. | 434/362 |
| 2012/0310667 A1 | 12/2012 | Altman et al. | 705/3 |
| 2012/0316897 A1 | 12/2012 | Hanina et al. | 705/3 |
| 2013/0030839 A1 | 1/2013 | Opfer et al. | 705/3 |
| 2013/0073343 A1* | 3/2013 | Richardson et al. | 705/7.38 |
| 2013/0138450 A1* | 5/2013 | Vigneux | 705/2 |
| 2013/0185096 A1* | 7/2013 | Giusti et al. | 705/3 |
| 2014/0081659 A1* | 3/2014 | Nawana et al. | 705/3 |

\* cited by examiner

APPARATUS AND METHOD FOR IMPROVING COMPLIANCE WITH A THERAPEUTIC REGIMEN

CROSS-REFERENCE TO RELATED APPLICATION(S)

This patent application is a continuation of, and therefore claims priority from, U.S. patent application Ser. No. 13/800,973 entitled Apparatus and Method for Improving Compliance with a Therapeutic Regimen filed on Mar. 13, 2013, which is hereby incorporated herein by reference in its entirety.

TECHNICAL FIELD

The present invention relates to therapeutic regimens, and more particularly to computer implemented methods for improving compliance with a therapeutic regimen.

BACKGROUND ART

It is known in the prior art to use computers to track physiological and pathological conditions of patients suffering from a condition.

SUMMARY OF THE EMBODIMENTS

In a first embodiment of the invention there is provided a computer-implemented method for improving compliance with a therapeutic regimen for each of a plurality of patients. The method of this embodiment includes:
for each patient:
receiving and storing at the server physiological data pertinent to such patient; receiving and storing at the server data characterizing a therapeutic regimen for such patient;
retrieving and using the physiological data pertinent to a medical condition of such patient to customize the therapeutic regimen for such patient;
causing presentation by the server to the patient via an application running on the mobile computing device, on at least a daily basis, of (i) an updated list of items to be performed by the patient on the date of presentation on the updated list and (ii) a region on a display of the mobile computing device for reporting performance of items on the updated list so as to cause sending by the mobile computing device to the server of patient compliance data; and
receiving at the server from the mobile computing device the patient compliance data, storing such data and using such data in calculating the updated list for presentation to the patient via the mobile computing device on a subsequent occasion;
wherein the server and the mobile computing device are in communication with each other over a first network that includes the internet.

In a related embodiment, the method further includes causing presentation by the server to the patient via the application running on the mobile computing device, on at least a daily basis, of (iii) a personalized comment reflective of the patient compliance data and configured to provide encouragement to the patient.

In another related embodiment, the method further includes causing presentation by the server to the patient via the application running on the mobile computing device, on at least a daily basis, of a statistical analysis of performance by the patient that provides at least a quantitative measure of an extent to which the patient has reached therapeutic goal.

Optionally, the method further includes causing presentation by the server to the patient via the application running on the mobile computing device, on at least a daily basis, of a statistical analysis of performance by the patient relative to the performance of others.

In yet another embodiment, the method further includes causing presentation by the server to the patient via the application running on the mobile computing device, on at least a daily basis, of a text interface by which the patient can initiate and receive textual communications with a health professional.

In yet another embodiment, the method further includes causing presentation by the server to the patient via the application running on the mobile computing device, on at least a daily basis, of a narrative report of patient activities including interactions with health professionals, specific actions by the patient relative to the regimen, and interactions with individuals in the patient's support network.

Alternatively or in addition, the method further includes causing presentation by the server to the patient via the application running on the mobile computing device, on at least a daily basis, of media content selected to assist the patient in achieving the goals of the therapeutic regimen.

Alternatively or in addition, the method further includes causing presentation by the server to the patient via the application running on the mobile computing device, on at least a daily basis, of media content selected to assist the patient in learning about the medical condition of the patient.

Also alternatively or in addition, the method further includes receiving at the server from the mobile computing device data, derived from at least one of accelerometer and GPS signals generated by the mobile computing device, characterizing patient physical activity as recorded by the application running on the mobile computing device.

Also alternatively or in addition, the method further includes causing presentation by the server to the patient via the application running on the mobile computing device, on at least a daily basis, of a voice interface by which the patient can initiate and receive voice communications with a health professional.

In another further embodiment, the method further includes causing presentation by the server to the patient via the application running on the mobile computing device, on at least a daily basis, of a video interface by which the patient can initiate and receive video communications with a health professional.

In another further embodiment, the method further includes causing presentation by the server to the patient via the application running on the mobile computing device, on at least a daily basis, of a self-assessment interface configured to obtain a self-assessment by the patient and to cause communication of the self-assessment to the server.

In another further embodiment, the method further includes causing presentation by the server to the patient via the application running on the mobile computing device, on at least a daily basis, of a point score for the patient based on a statistical analysis of activities by the patient demonstrating progress towards goals of the therapeutic regimen, such activities including at least two members of the group consisting of compliance with the regimen, demonstration of understanding of the medical condition, consistency of performance, and interactions with the patient's support network and with other patients.

In another further embodiment, the method further includes causing presentation, by the server, to a computer system of a health practitioner, such computer system being in communication with the server over a second network that includes the internet, of a patient status listing, such listing including, for each patient thereon, an indicator dynamically characterizing, in real time, extent of compliance of such patient with goals of the therapeutic regimen customized for such patient and wherein such listing is sorted in reverse order according to extent of compliance.

In a further related embodiment, such listing is provided with a patient detail interface by which the health practitioner can graphically select a particular patient in the listing and thereupon obtain additional information concerning such patient including compliance data, physiological data, and physical activity of such patient. Optionally, such listing is provided with a patient regimen interface by which the health professional can modify the regimen customized for such patient with a view to improving such patient's progress toward goals of the therapeutic regimen.

In another further related embodiment, receiving and storing at the server physiological data pertinent to such patient includes receiving and storing such data from at least one third party application.

In another embodiment, the invention provides a computer-implemented method of developing a therapeutic regimen customized for a given patient with a specific medical condition. The method of this embodiment includes storing data in a health state database that characterizes a series of health states defining a natural history of the condition, wherein each health state is characterized by a set of physiological and pathological parameter values; storing in a regimen database a distinct therapeutic regimen for each health state in the series; storing the physiological and pathological parameter values applicable to the current medical condition of the given patient; processing the physiological and pathological parameter values applicable to the given patient and accessing the health state database so as to characterize the patient's current health state; and processing the current health state of the patient and accessing the regimen database to retrieve the therapeutic regimen for the patient based on the patient's current health state. Optionally, the method further includes customizing the retrieved therapeutic regimen based on the specific physiological and pathological parameter values applicable to the current medical condition of the given patient. Alternatively or in addition, the method includes customizing the retrieved therapeutic regimen based on an input provided by a health professional.

In another embodiment, the invention provides a computer-implemented method of enhancing a support network of a given patient in a therapeutic regimen for a medical condition of the patient. The method of the embodiment includes accessing a database of pathological data for patients to identify pathological data pertinent to the given patient; using the identified data, searching in the database to identify a set of other patients having similar pathological data; and causing transmission, to a mobile computing device of the given patient, of a message introducing a member of the identified set to the given patient. Optionally, accessing the database includes accessing the database also to identify demographic data pertinent to the given patient, and searching includes searching to identify a set of other patients having similar pathological and demographic data. Optionally, accessing the database includes accessing the database also to identify location data of the given patient, and searching includes searching to identify a set of other patients having similar pathological and location data. Optionally, location data includes at least one of (i) GPS data gathered from mobile computing devices of patients and stored in the database and (ii) residential addresses of patients. Optionally, accessing the database includes accessing the database also to identify regimen compliance data of the given patient, and searching includes searching to identify a set of other patients having similar pathological and regimen compliance data.

In yet another embodiment there is provided a non-transitory digital storage medium encoded with instructions that, when loaded into a computer causes the computer to implement one of the foregoing method embodiments. A distinct storage medium embodiment is associated with each distinct one of the foregoing method embodiments.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Definitions

As used in this description and the accompanying claims, the following terms shall have the meanings indicated, unless the context otherwise requires:

A "mobile computing device" means any of a smartphone, a tablet computer, a personal digital assistant, or other portable computing device configured to connect directly or indirectly to the internet, including via a wireless telephone data connection, or a WiFi or Bluetooth or other wireless connection to an internet-coupled access device.

A "computer system" means any desktop computer or laptop computer having a connection to the internet, or a mobile computing device.

A patient with a "specific medical condition" includes an undiagnosed patient at risk of developing the specific medical condition as well as a patient diagnosed with the specific medical condition.

A particular "health state" of a patient with a medical condition is a characterization of the patient's physiological and pathological status in relation to a series of health states defining the natural history of the condition.

A therapeutic "regimen" for a medical condition of a patient is a collection of therapeutic activities, recommended to the patient, designed to improve the health state of the patient; such activities can include medication compliance, physical activity, health behavior change (including diet, smoking cessation, alcohol moderation, and stress management), communication with health professionals and peers, compliance with a schedule of in-person visits with health professionals, and screening for associated conditions.

A "set" includes at least one member.

A "third party application," in the context of a server that communicates via an application running on a mobile computing device of a patient for the purpose of enhancing compliance of the patient with a therapeutic regimen, is a data source that is controlled by an institution other than an institution controlling operation of the server.

Figure 1:
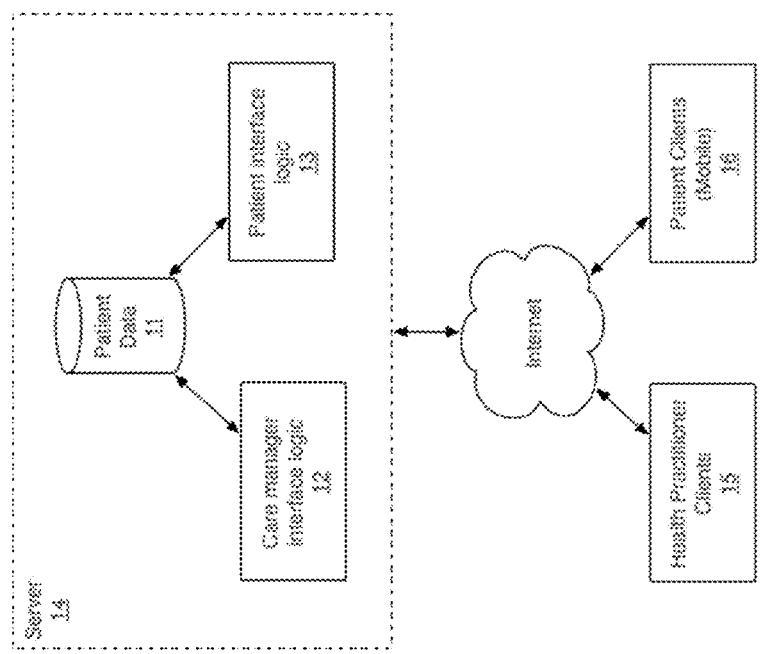
FIG. 1 is a block diagram of system architecture for an exemplary embodiment of the present invention.

FIG. 1 is a block diagram of system architecture for an exemplary embodiment of the present invention. A server 14 handles communication over the internet with computer systems of health practitioners as clients of the server 14. These client computing devices are collectively shown as item 15 in FIG. 1. Similarly the server 14 handles communication over the internet with mobile computing devices of patients which are here collectively shown as item 16 in FIG. 1. As can be seen in FIG. 1, the server 14 handles patient data in a database 11, and this database is accessed by logic operative in communications with the health practitioner clients 15 and we identify this logic as care manager interface logic 12 in FIG. 1. Similarly the server 14 accesses patient data in database 11 using logic operative in communication with the patient client 16 and we identify this logic as patient interface logic 13.

Figure 2:
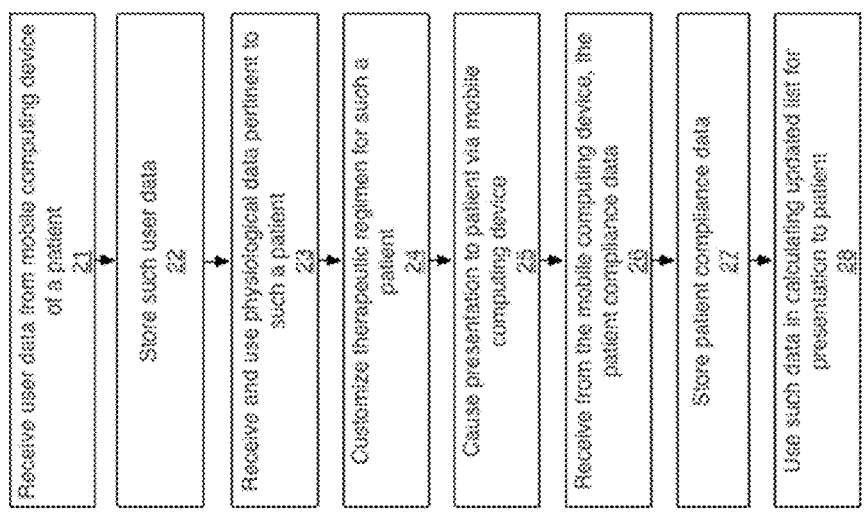
FIG. 2 is a block diagram illustrating logical flow of the embodiment of FIG. 1.

FIG. 2 is a block diagram illustrating logical flow of the embodiment of FIG. 1 for an exemplary embodiment of the present invention. In this embodiment, the server receives user data patient data in process 21 from the application running on the patient's mobile computing device and then stores this data in a patient database in process 22. Using this stored patient data, the server retrieves the data pertinent to a particular patient in process 23 in order to customize the therapeutic regimen for such patient in process 24. The server then causes presentation of the therapeutic regimen in process 25 to the application running on the patient's mobile computing device, which in one embodiment, can be represented as an itemized list of "to-do" items based on the patient's therapeutic regimen. The server receives data from a patient's interaction with the application running on the patient's mobile device, which in one embodiment, constitutes data about a patient's compliance with the therapeutic regimen. After receiving this data, the server stores in it in a patient database in process 27 and uses this data in process 28 to calculate the updated itemized list of "to-do" items for presentation to the patient.

Figure 3:
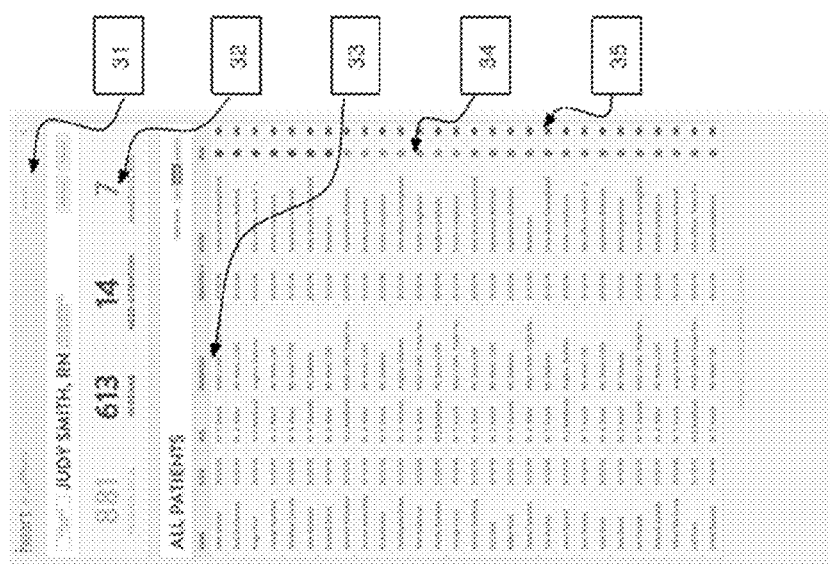
FIG. 3 is a representation, in accordance with an embodiment of the present invention, of web page content served to a computer system of a health professional, presenting the health professional's dashboard with an overview of all patients.

FIG. 3 is a representation, in accordance with an embodiment of the present invention, of web page content served to a computer system of a health professional, presenting the health professional's dashboard with an overview of all patients. At the top of the display is search box 31 which enables a health professional to search amongst a set of patients to identify a subset of patients with common attributes. Priority bar 32 displays summary statistics regarding number of patients by priority category to enable the health professional to graphically select patients by priority category. Below this patients are listed and organized by attributes in table 33. Each patient is given a priority, according to an indicator 34 which is red, yellow or green depending on the priority with which the patient needs to be attended to. The server causes presentation of all data with respect to priority. Message element 35 enables the health professional to send a message to the patient without the need for further inspection of the patient's data. The health professional has other ways of messaging the patient as described in FIG. 4.

Figure 4:
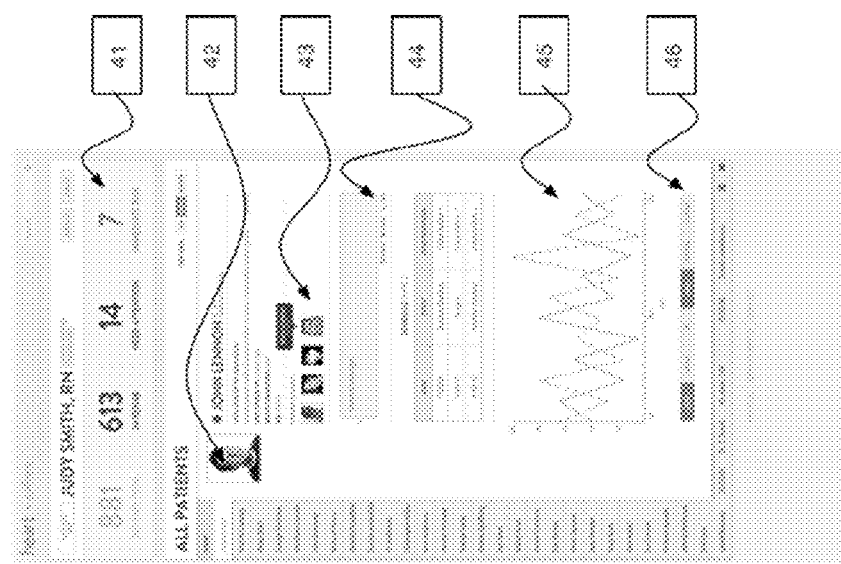
FIG. 4 is a representation, of web page content, served to a computer system of a health professional, presenting detail of a patient that has been graphically selected from the displayed web page of FIG. 3.

FIG. 4 is a representation, of web page content, served to a computer system of a health professional, presenting detail of a patient that has been graphically selected from the displayed web page of FIG. 3. Priority bar 41 displays summary statistics regarding number of patients by priority category to enable the health professional to graphically select patients by priority category. Image 42 is an image or icon representing the patient. Image collection 43 is a collection of images of the patient's support network. The patient's support network includes friends, family and other care providers. Message element 44 when graphically selected enables a health professional to send a text, image or video message to a patient's mobile computing device to optimize compliance with the regimen optimized for the patient. Graph element 45 allows historical patient physiological data to be displayed for the health professional according to attributes selected in data selector 46.

Figure 5:
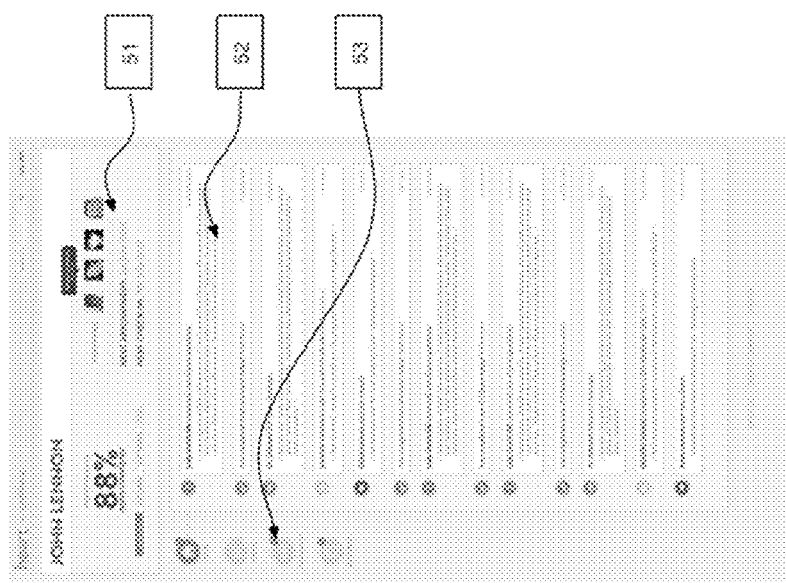
FIG. 5 is a representation, of web page content, served to a computer system of the patient of FIG. 4, presenting for benefit of the patient a historical view of previous activities of the patient in relation to a regimen that has been customized for the patient.

FIG. 5 is a representation, of web page content, served to a computer system of the patient of FIG. 4, presenting for benefit of the patient a historical view of previous activities of the patient in relation to a regimen that has been customized for the patient. At the top of the display is header 51 which identifies the most important information regarding the patient's regimen. Examples of such information include but are not limited to summary statistics pertaining to compliance with the regimen, last contact with a health professional, next content with a health care professional and details of the patient's support network. As detailed previously, the patient's support network includes friends, family and other care providers. Below this is patient feed 52 which is a historical view of previous activities of the patient in relation to a regimen that has been customized for the patient. Tab 53 enables a patient to navigate between different views of the web page as described in FIG. 6 (question and answer forum) and FIG. 7 (resources.)

Figure 6:
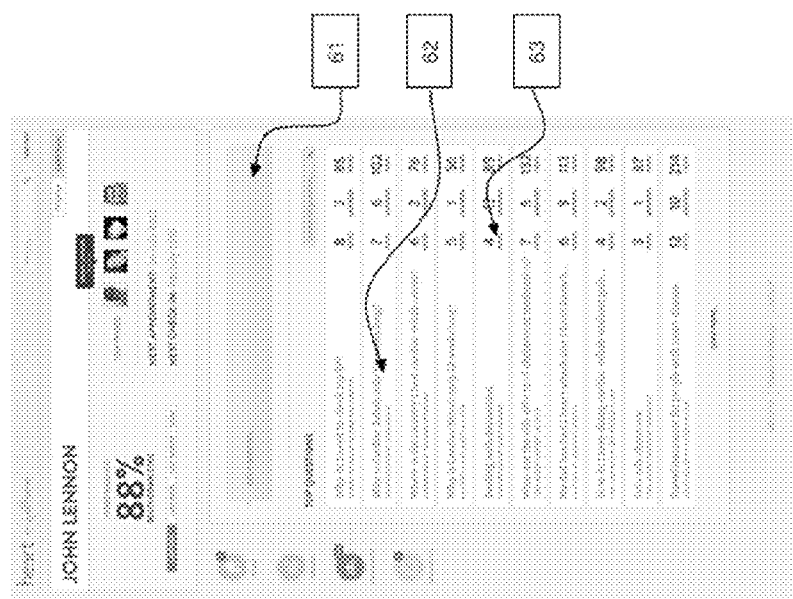
FIG. 6 is a representation, of web page content, served to a computer system of the patient of FIG. 5, presenting for benefit of the patient a question and answer forum pertaining to the regimen that has been optimized for the benefit of the patient.

FIG. 6 is a representation, of web page content, served to a computer system of the patient of FIG. 5, presenting for benefit of the patient a question and answer forum pertaining to a condition of the patient. At the top of the page is text entry element 61 which enables a patient to ask a question of a set of patients who have the same or similar medical conditions. The questions 62 are arranged in a table with interaction statistics 63 describing how many times a question has been viewed, answered and voted up by other patients.

Figure 7:
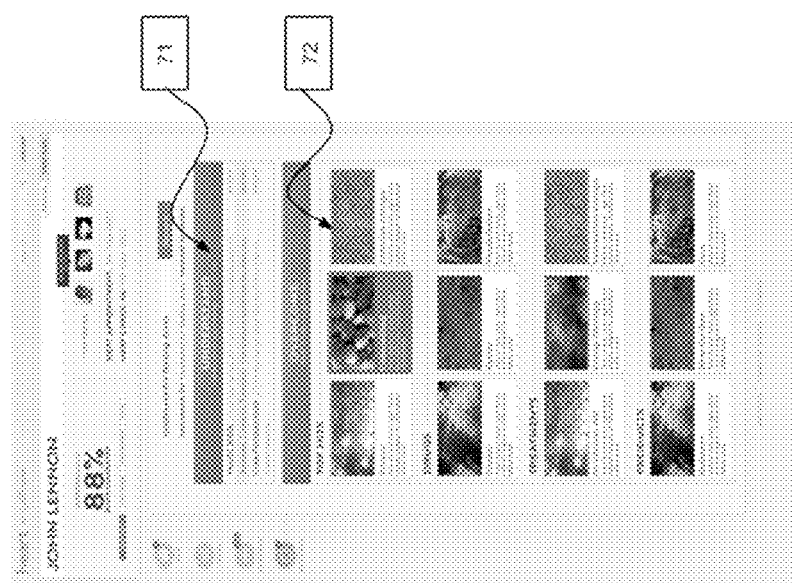
FIG. 7 is a representation, of web page content, served to a computer system of the patient of FIG. 5, presenting for benefit of the patient recommended content in thematic areas (such as medication, treatment and recommended products.)

FIG. 7 is a representation, of web page content, served to a computer system of the patient of FIG. 5, presenting for benefit of the patient recommended content in thematic areas (such as medication, treatment and recommended products.) At the top of the display is Table 71 which displays medical guidelines served according to the patient's compliance with the regimen. The purpose of the guidelines is to display to the patient the evidence based standards of care that underpin the regimen that the patient is following. Table 72 features served content recommended for the patient based on their compliance with the therapeutic regimen. This content includes educational material pertaining to medication and treatments and products, which are provided to optimize the compliance of the patient with the regimen.

Figure 8:
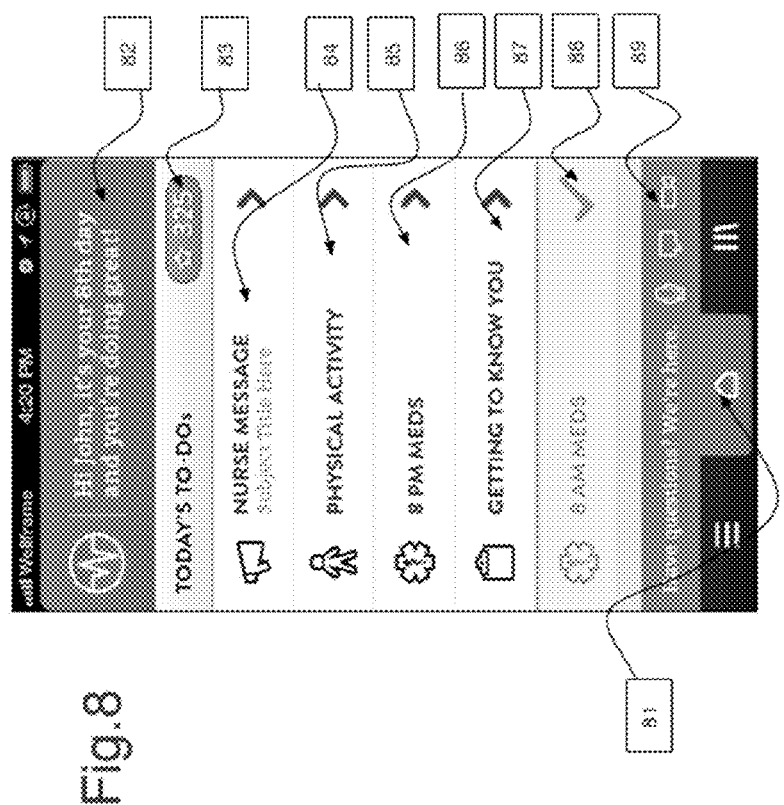
FIG. 8 is a representation of a display, on a mobile computing device of a patient running a dedicated application, of content served to the mobile computing device and configured to enhance compliance of a patient with a customized regimen, the content here presenting the patient's to-do list with a points indicator, in accordance with an exemplary embodiment of the present invention.

FIG. 8 is a representation of a display, on a mobile computing device of a patient running a dedicated application, of content served to the mobile computing device and configured to enhance compliance of patient with a customized regimen, the content here presenting the patient's to-do list with a points indicator, in accordance with an exemplary embodiment of the present invention. In this figure is represented the home screen seen by the patient when the patient opens the application running on the patient's mobile computing device. This screen is additionally accessible from the Home Tab 81. At the top of this display is a message 82 intended to give the patient feedback on progress of the patient toward goals of the therapeutic regimen. Below the message 82 is a point total 83, which provides to the patient a score that is a measure of the patient's compliance with the regimen. Below the point total 83 is an example set of to do items generated by the server to improve compliance with the therapeutic regimen optimized for the patient including message notification 84, a prompt to track physical activity 85, a medication reminder 86 and survey 87. Other to-do items could include questions regarding nutrition, reminders regarding behavior change (smoking cessation, weight loss, stress reduction, alcohol moderation), prompts to track physical activity and appointment reminders. Graphically selecting items 83 to 87 or other such to-do list items will cause presentation of more detailed views as displayed in FIGS. 10-16, 26-30 and 31-38. Below the to-do list items 82, 83, 84, 85, 86, 87 and 88 is help element 89, which enables the patient to contact a health professional regarding the therapeutic regimen that has been optimized for the patient. Graphically selecting this notification will cause presentation of the displays represented in FIGS. 12, 13 and 14.

Figure 9:
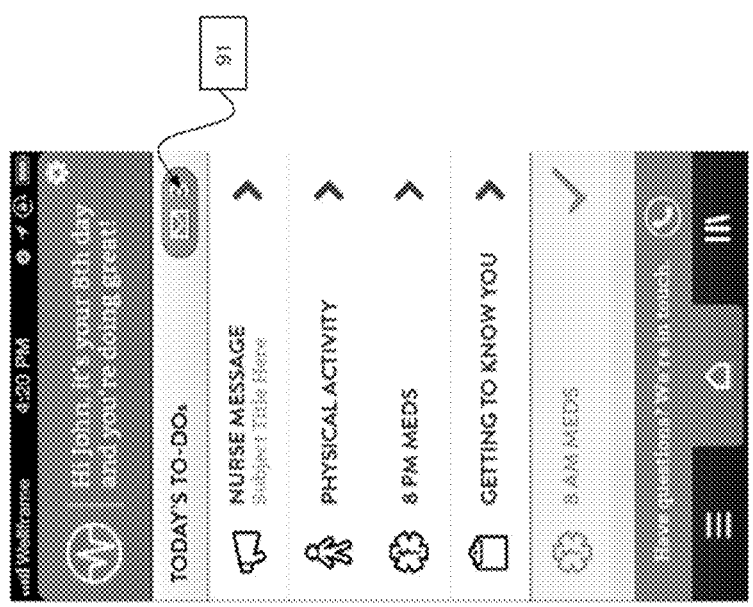
FIG. 9 is a representation of a display, on the mobile computing device of the patient of FIG. 8, wherein the served content here presents the patient's to-do list with a message indicator.

FIG. 9 is a representation of a display, on the mobile computing device of the patient of FIG. 8, wherein the served content here presents the patient's to-do list with a message indicator. Graphically selecting message indicator 91 will cause presentation of FIG. 15.

Figure 10:
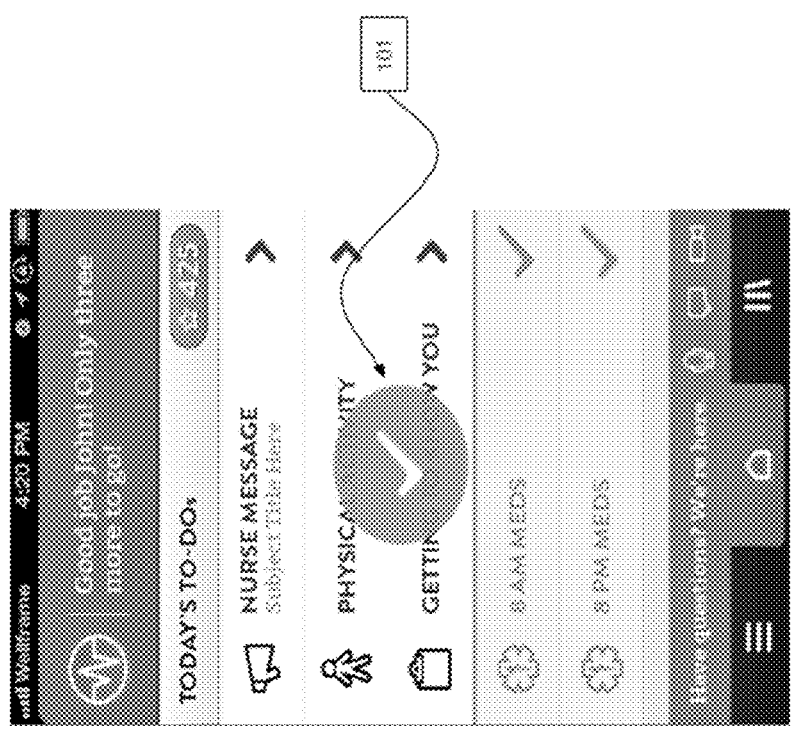
FIG. 10 is a representation of a display, on the mobile computing device of the patient of FIG. 8, wherein the served content here presents the patient's to-do list with feedback regarding task completion.

FIG. 10 is a representation of a display, on the mobile computing device of the patient of FIG. 8, wherein the served content here presents the patient with feedback regarding to-do list item completion. Visual feedback 101 is accompanied by tactile feedback (vibration) and auditory feedback (a bell sound) presented on the mobile computing device of the patient.

Figure 11:
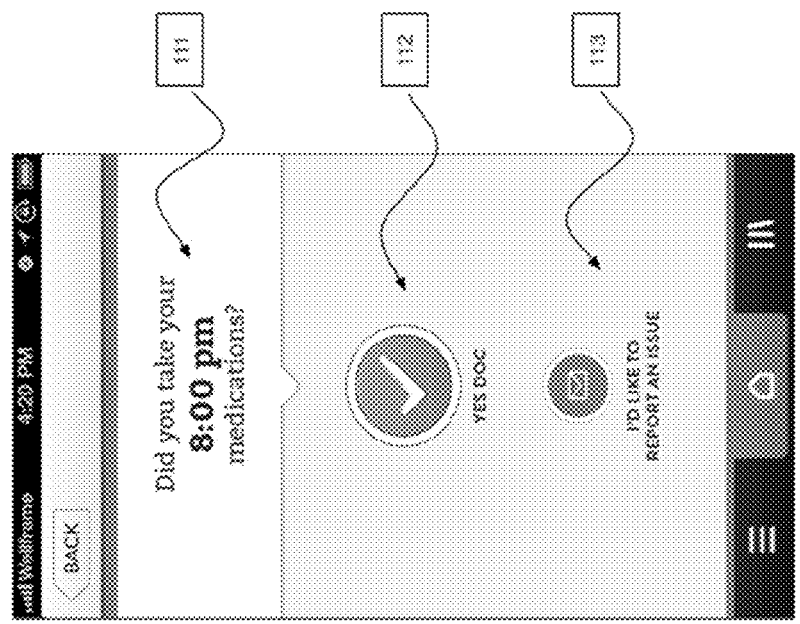
FIG. 11 is a representation of a display, on the mobile computing device of the patient of FIG. 8, wherein the served content here presents a medication reminder that is displayed when medication reminder 86 from FIG. 8 is graphically selected from the to-do list.

FIG. 11 is a representation of a display, on the mobile computing device of the patient of FIG. 8, wherein the served content here presents a medication reminder that is displayed when medication reminder 86 from FIG. 8 is graphically selected from the to-do list. At the top of this display is medication reminder question 111. Below medication reminder 111 are answer options 112 and 113. Graphically selecting answer option 112 will cause an affirmative response to be returned to the server. Graphically selecting answer option 113 will cause presentation of an entry element for the patient to report a problem pertaining to the patient's medication to the server.

Figure 12:
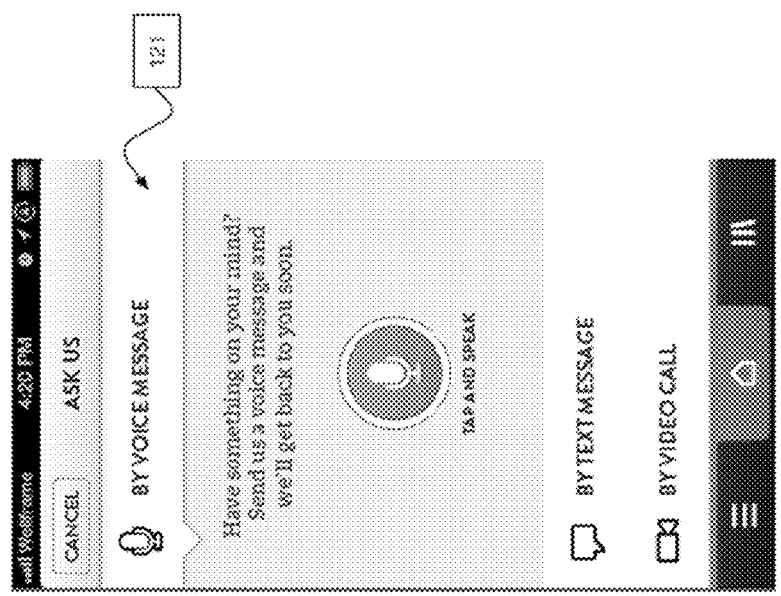
FIG. 12 is a representation of a display, on the mobile computing device of the patient of FIG. 8, wherein the served content here presents a means of a patient contacting a health professional by voice message that is displayed when medication reminder 86 is graphically selected from FIG. 8.

FIG. 12 is a representation of a display, on the mobile computing device of the patient of FIG. 8, wherein the served content here presents a means of a patient contacting a health professional by voice message that is displayed when medication reminder 86 is graphically selected from FIG. 8. At the top of this display is a voice message prompt 121 which invites a patient to record a voice message pertaining to their condition to be sent to a health professional.

Figure 13:
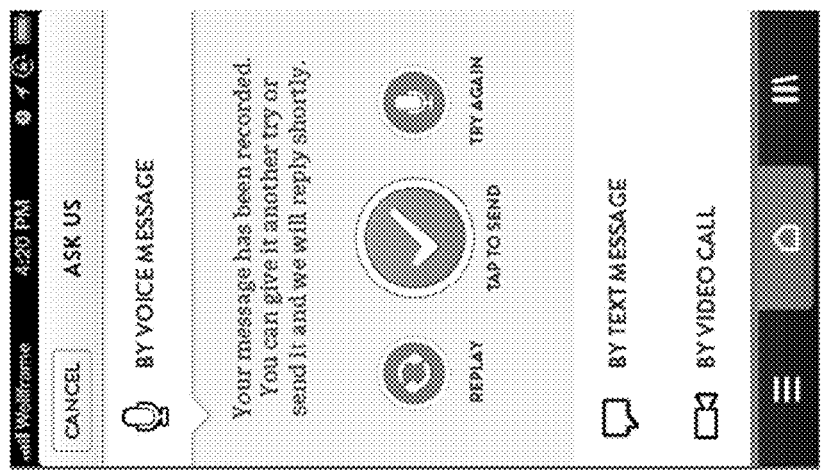
FIG. 13 is a representation of a display, on the mobile computing device of the patient of FIG. 8, wherein the served content here presents a means of the patient reviewing and re-recording a voice message from FIG. 12 prior to sending to a health professional.

FIG. 13 is a representation of a display, on the mobile computing device of the patient of FIG. 8, wherein the served content here presents a means of a patient reviewing and re-recording a voice message from FIG. 12 prior to sending to the server.

Figure 14:
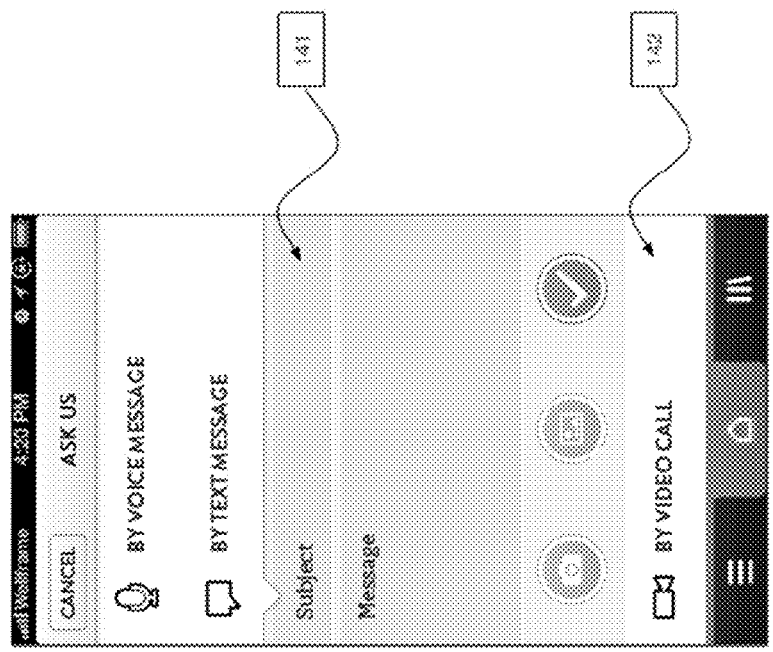
FIG. 14 is a representation of a display, on the mobile computing device of the patient of FIG. 8, wherein the served content here presents a means of the patient contacting a health professional by text.

FIG. 14 is a representation of a display, on the mobile computing device of the patient of FIG. 8, wherein the served content here presents a means of a patient contacting a health professional by text. Text entry box 141 allows a patient to enter text information and attach additional photographic material that can be sent to the server. Prompt 142 is a video call element which when graphically selected opens a video conferencing client on the mobile computing device of the patient.

Figure 15:
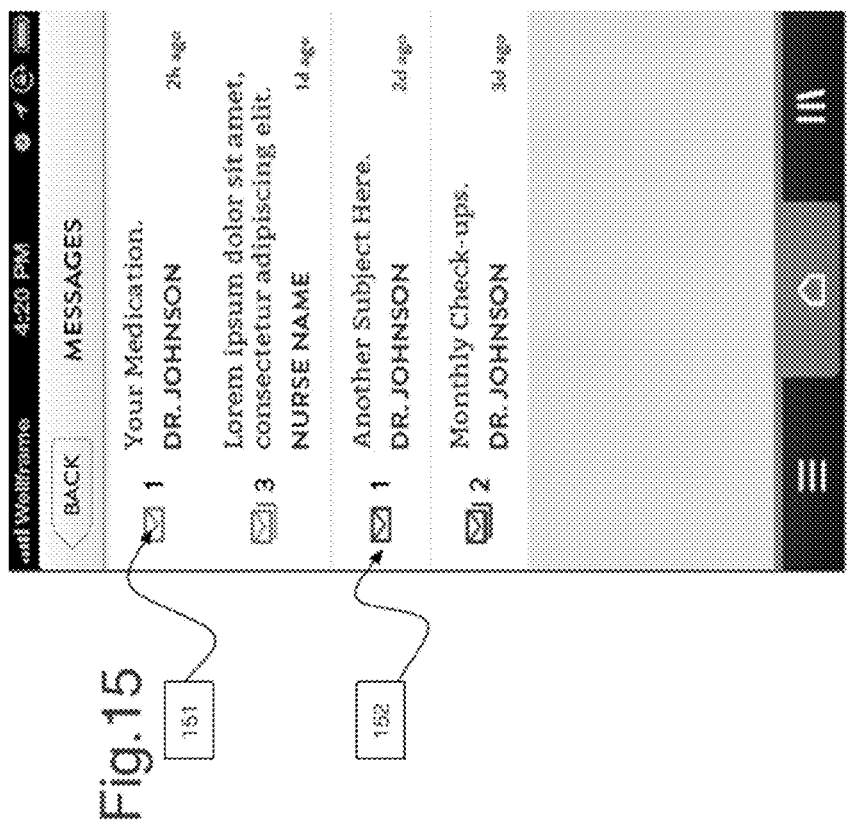
FIG. 15 is a representation of a display, on the mobile computing device of the patient of FIG. 8, wherein the served content here presents a list of messages consisting of a plurality of separate message threads for the benefit of the patient to improve compliance with the therapeutic regimen optimized for the patient.

FIG. 15 is a representation of a display, on the mobile computing device of the patient of FIG. 8, wherein the served content here presents a list of messages consisting of a plurality of separate message threads for the benefit of the patient to improve compliance with the therapeutic regimen optimized for the patient. Unread message 151 informs the patient of a new unread message. Read message icon 152 informs the patient of a message that was previously read and remains available for the benefit of the patient to improve compliance with the therapeutic regimen.

Figure 16:
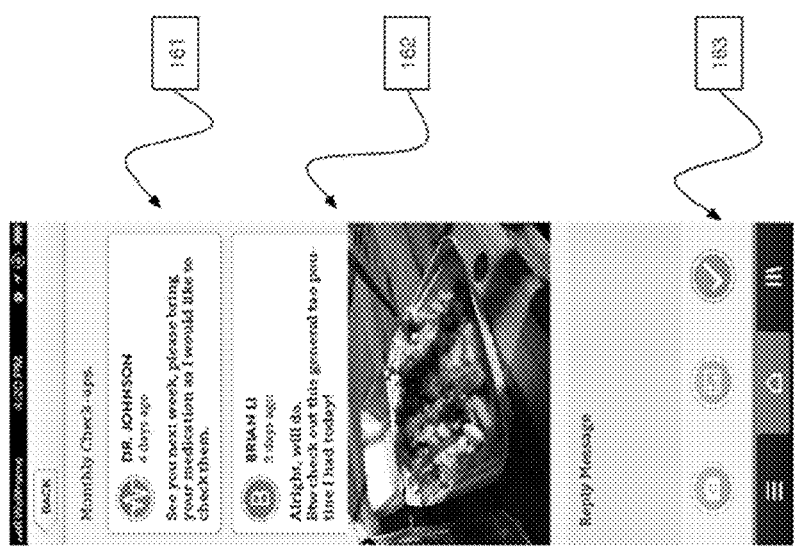
FIG. 16 is a representation of a display, on the mobile computing device of the patient of FIG. 8, wherein the served content here presents an expanded view of an individual message thread for the patient.

FIG. 16 is a representation of a display, on the mobile computing device of the patient of FIG. 8, wherein the served content here presents an expanded view of an individual message thread for the benefit of the patient. Message 161 is a text message. Message 162 is a text and photographic message. Text entry box 163 allows a message and optional attached photographic material to be sent to the server.

Figure 17:
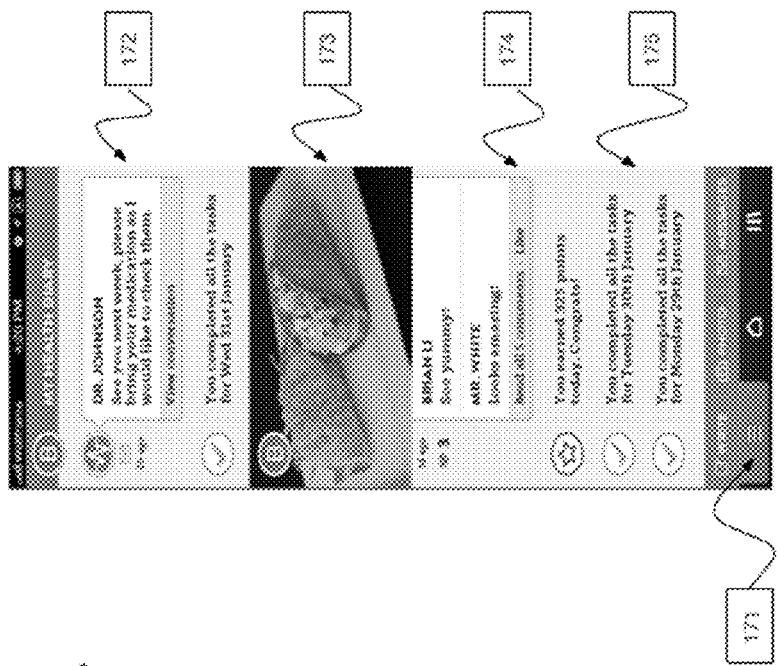
FIG. 17 is a representation of a display, on a mobile computing device of a patient running a dedicated application, of content served to the mobile computing device and configured to enhance compliance of the patient with a customized regimen, the content here presenting for benefit of the patient a historical view of previous activities of the patient in relation to a regimen that has been customized for the patient in accordance with an exemplary embodiment of the present invention.

FIG. 17 is a representation of a display, on a mobile computing device of a patient running a dedicated application, of content served to the mobile computing device and configured to enhance compliance of the patient with a customized regimen, the content here presenting for benefit of the patient a historical view of previous activities of the patient in relation to a regimen that has been customized for the patient in accordance with an exemplary embodiment of the present invention. The historical view of previous activities of the patient in relation to a regimen that has been customized for the patient is accessible by graphic selection of Feed Tab 171. At the top of this display is health professional message 172. Below this is photograph 173 previously taken by the patient and commented on by the patient's support network in comment 174. Item 175 presents a summary statistic of historical compliance with the regimen.

Figure 18:
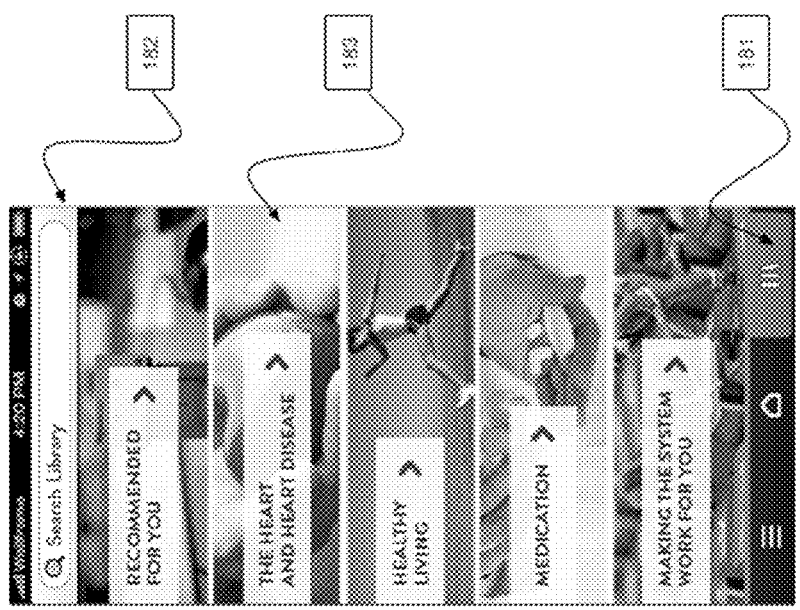
FIG. 18 is a representation of a display, on a mobile computing device of a patient running a dedicated application, of content served to the mobile computing device and configured to enhance compliance of the patient with a customized regimen, the content here presenting for benefit of the patient recommended education material and education material in thematic areas in accordance with an exemplary embodiment of the present invention.

FIG. 18 is a representation of a display, on a mobile computing device of a patient running a dedicated application, of content served to the mobile computing device and configured to enhance compliance of the patient with a customized regimen, the content here presenting for benefit of the patient recommended education material and education material in thematic areas in accordance with an exemplary embodiment of the present invention. Search box 182 enables a patient to search the store of education material on the server. Header 183 when graphically selected allows a patient to access more educational material within a thematic area.

Figure 19:
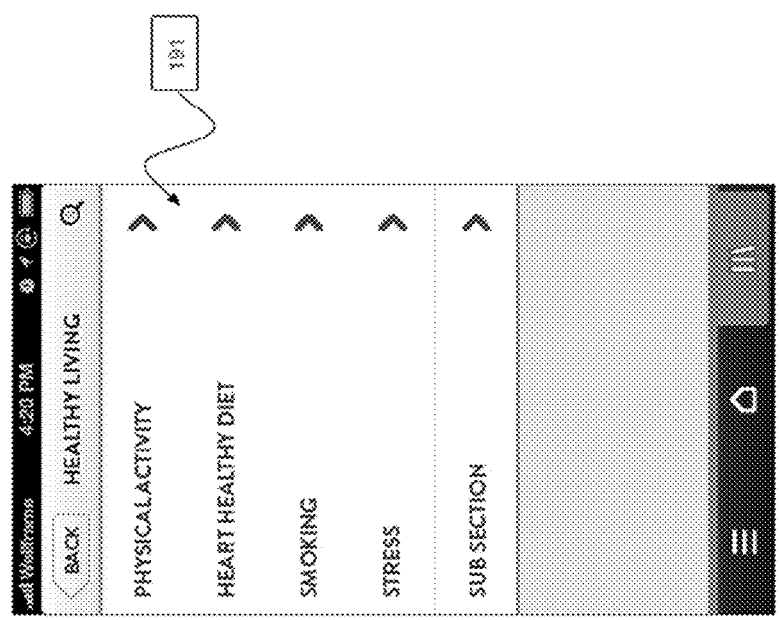
FIG. 19 is a representation of a display, on the mobile computing device of the patient of FIG. 18, wherein the served content here presents an expanded view of one thematic area with content further organized in sub-categories for the benefit of the patient.

FIG. 19 is a representation of a display, on the mobile computing device of the patient of FIG. 18, wherein the served content here presents an expanded view of a thematic area with content further organized into sub-categories for the benefit of the patient. Sub-category 191 when graphically selected displays further nested categories and individual items of educational material.

Figure 20:
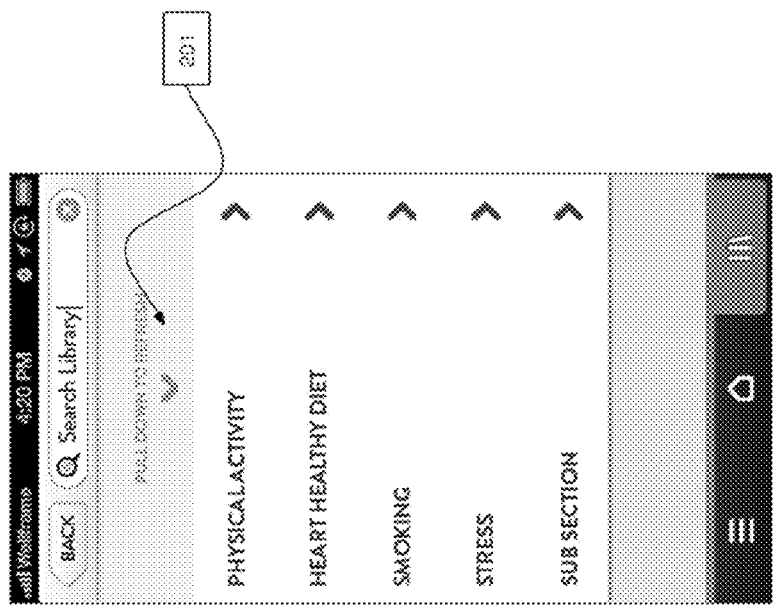
FIG. 20 is a representation of a display, on the mobile computing device of the patient of FIG. 18, wherein the served content here presents an expanded view of a thematic area with content further organized in sub-categories with an element which when graphically selected allows the content to be refreshed for benefit of the patient.

FIG. 20 is a representation of a display, on the mobile computing device of the patient of FIG. 18, wherein the served content here presents an expanded view of a thematic area with content further organized in sub-categories with an element which when graphically selected allows the content to be refreshed for benefit of the patient. Refresh element 201 when graphically selected allows the content to be reloaded from the server for the benefit of the patient.

Figure 21:
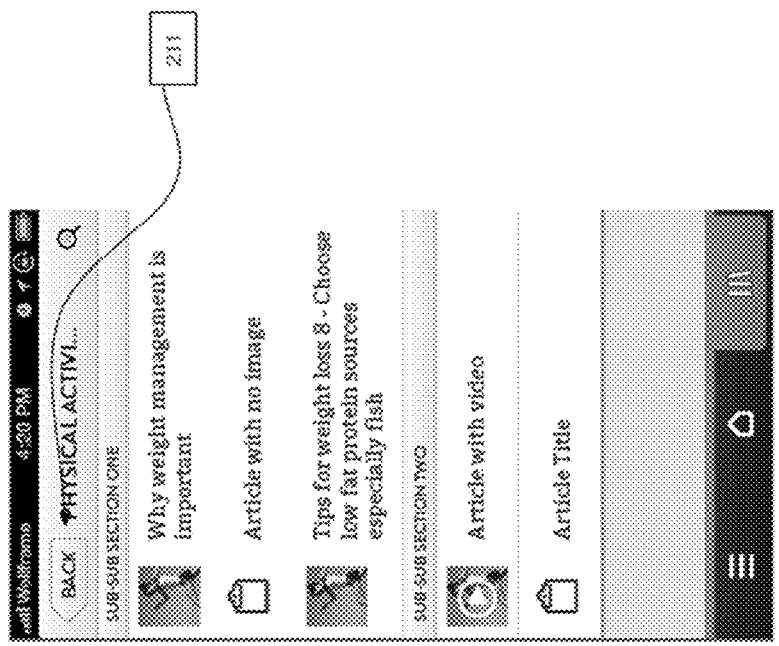
FIG. 21 is a representation of a display, on the mobile computing device of the patient of FIG. 18, wherein the served content here presents an expanded view of a sub-category with content organized into further sub-categories for benefit of the patient.

FIG. 21 is a representation of a display, on the mobile computing device of the patient of FIG. 18, wherein the served content here presents an expanded view of a sub-category with content organized into further sub-categories for the benefit of the patient. Back button 211 enables the patient to return to the previous level as displayed in FIG. 19.

Figure 22:
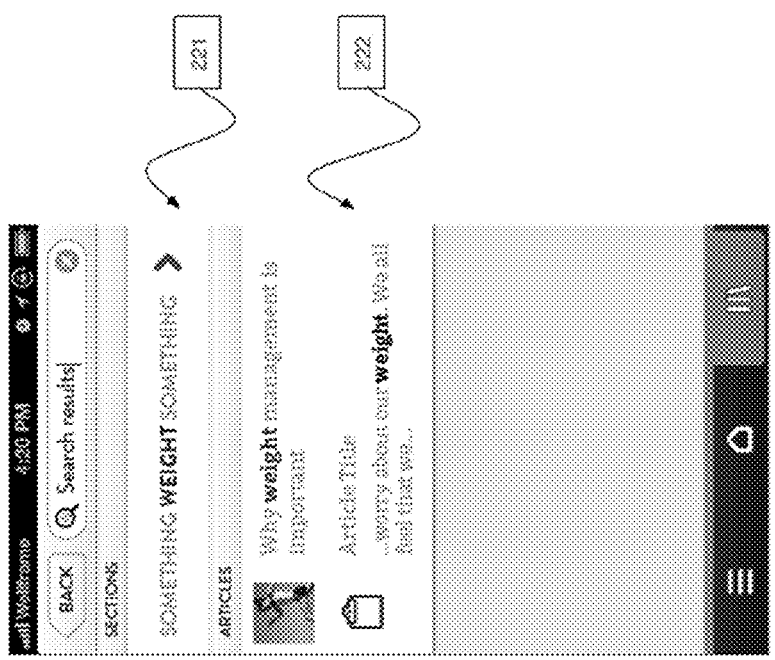
FIG. 22 is a representation of a display, on the mobile computing device of the patient of FIG. 18, wherein the served content here presents results of a search for benefit of the patient.

FIG. 22 is a representation of a display, on the mobile computing device of the patient of FIG. 18, wherein the served content here presents results of a search for the benefit of the patient. Content herein presented is organized in a number of ways including by section header 221 and by a list of articles 222.

Figure 23:
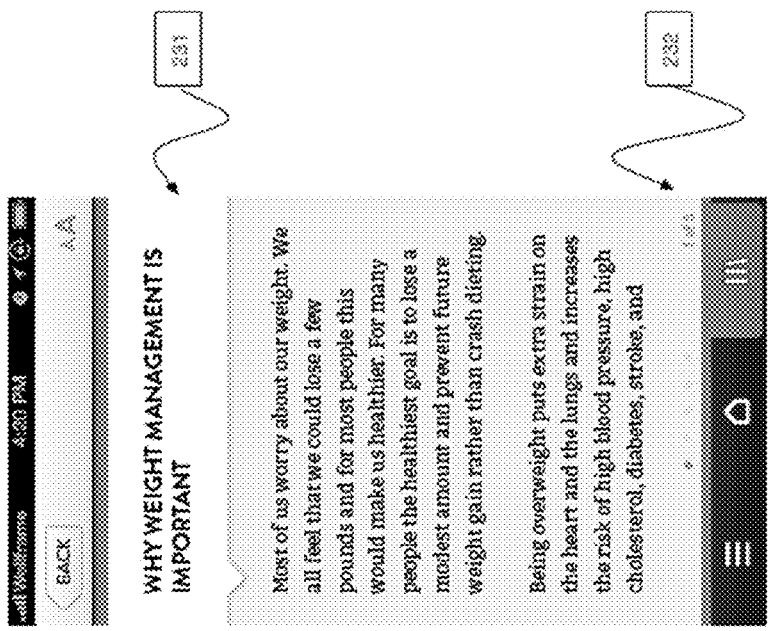
FIG. 23 is a representation of a display, on the mobile computing device of the patient of FIG. 18, wherein the served content here presents a text document with health education material presented for benefit of the patient.

FIG. 23 is a representation of a display, on the mobile computing device of the patient of FIG. 18, wherein the served content here presents a text document with health education material presented for the benefit of the patient. Heading 231 is the heading of the article. Navigation element 232 orients the patient as to which page of the article the patient is reading and how many pages are remaining.

Figure 24:
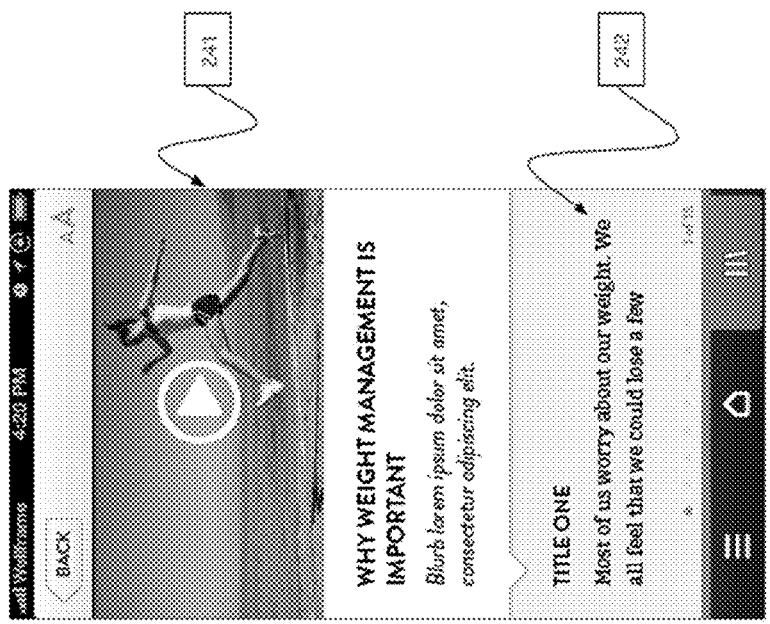
FIG. 24 is a representation of a display, on the mobile computing device of the patient of FIG. 18, wherein the served content here presents a video item with health education material presented for the benefit of the patient.

FIG. 24 is a representation of a display, on the mobile computing device of the patient of FIG. 18, wherein the served content here presents a video item with health education material presented for the benefit of the patient. At the top of this display is embedded video player 241. Below this is complementary written health education content content 242 displayed for the benefit of the patient to improve compliance with the regimen.

Figure 25:
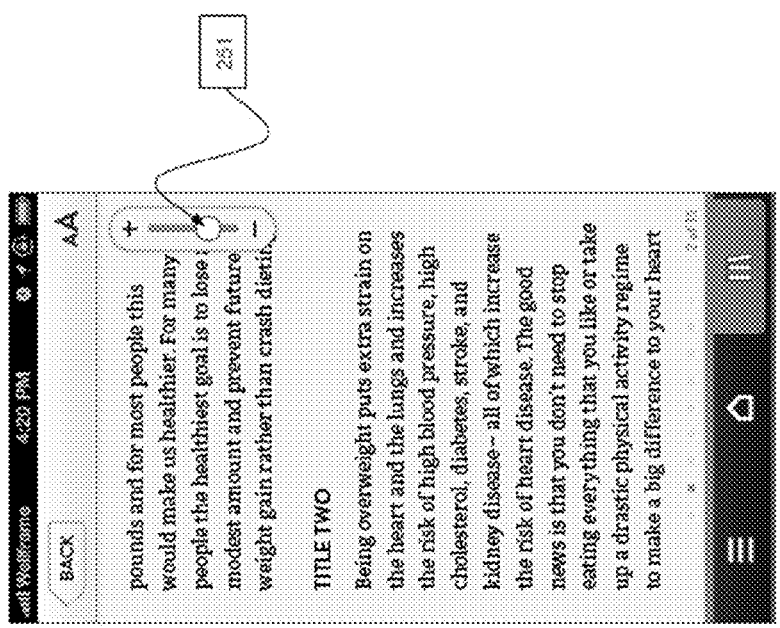
FIG. 25 is a representation of a display, on the mobile computing device of the patient of FIG. 18, wherein the served content here presents a text document with health education content presented for benefit of the patient where the text size is modifiable from the dedicated application running on the mobile computing device.

FIG. 25 is a representation of a display, on the mobile computing device of the patient of FIG. 18, wherein the served content here presents a text document with health education content presented for the benefit of the patient where the text size is modifiable from the dedicated application running on the mobile computing device. Slider 251 allows the patient to change the size of the text to suit their visual acuity needs and thereby improve compliance with the regimen that has been customized for the benefit of the patient.

Figure 26:
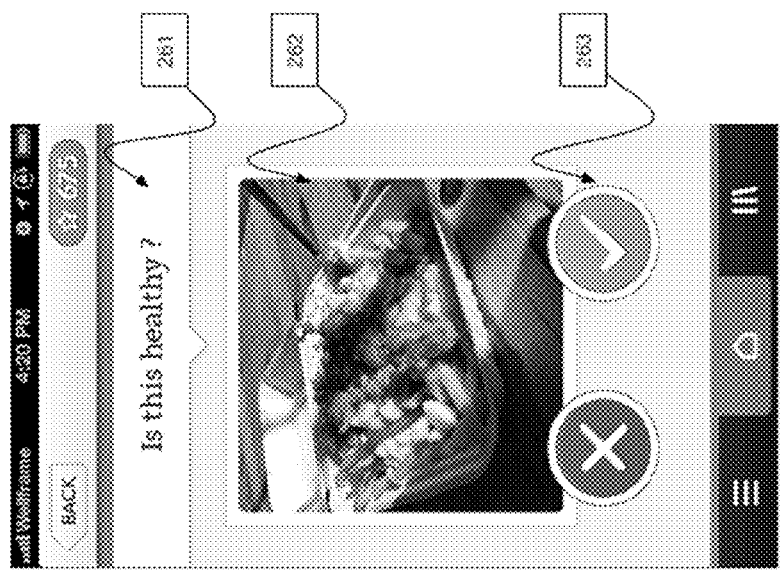
FIG. 26 is a representation of a display, on the mobile computing device of the patient of FIG. 8, wherein the served content here presents a question regarding the patient's knowledge of the patient's condition and it's treatment.

FIG. 26 is a representation of a display, on the mobile computing device of the patient of FIG. 8, wherein the served content here presents a question regarding the patient's knowledge of the patient's condition and it's treatment. Question 261 is posed to the patient. Photo 262 is the complement of question 261 and displays a health education item pertaining to achieving the goals of the therapeutic regimen. Answer elements 263 enable the patient to select multiple choice items to be sent to the server.

Figure 27:
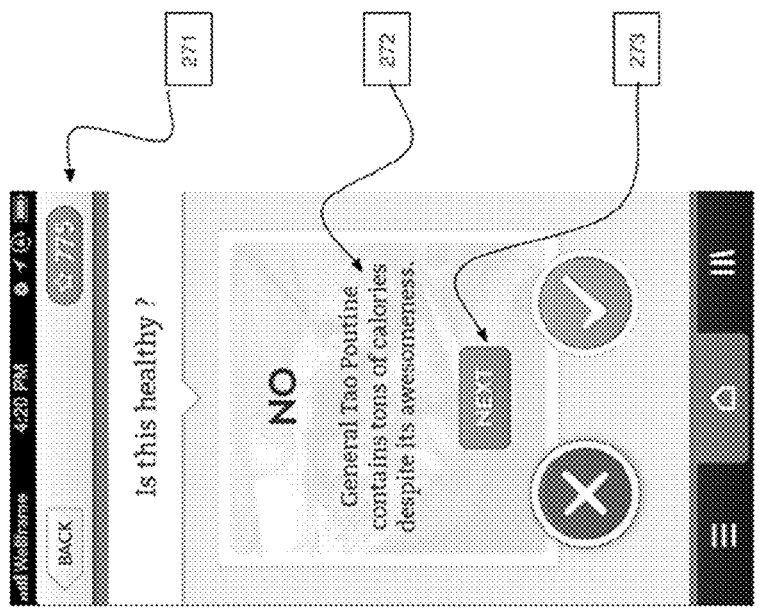
FIG. 27 is a representation of a display, on the mobile computing device of the patient of FIG. 8, wherein the served content here presents an answer to the question asked with learning material presented for the benefit of the patient.

FIG. 27 is a representation of a display, on the mobile computing device of the patient of FIG. 8 and FIG. 26, wherein the served content here presents an answer to the question asked with learning material presented for the benefit of the patient. Point indicator 271 displays a total of points gained from answering this and similar questions and completing to-do items configured to enhance compliance of a patient with a customized regimen. Feedback item 272 is the answer to question 261 presented to the patient to enhance compliance of the patient with a customized regimen. Next button 273 enables a patient to answer more questions of the type 261 to gain more points.

Figure 28:
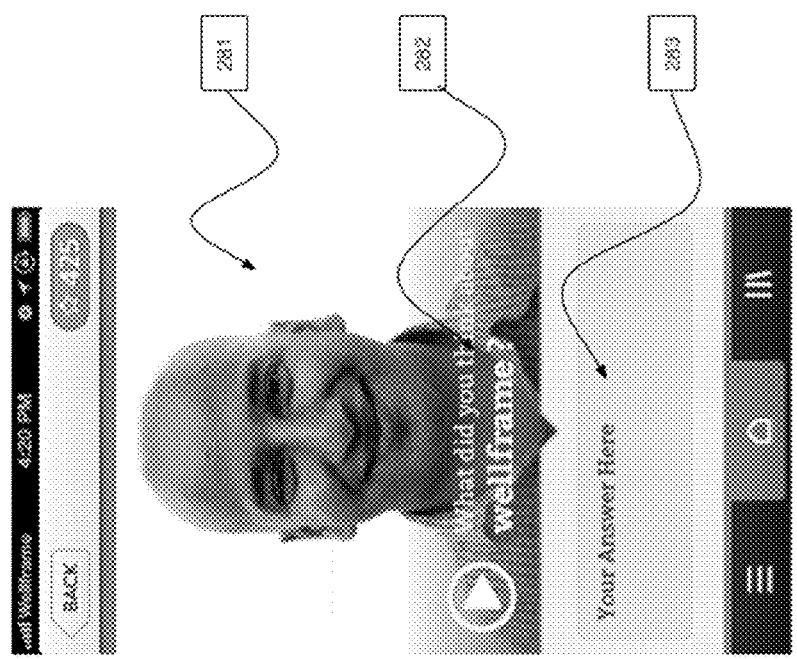
FIG. 28 is a representation of a display, on the mobile computing device of the patient of FIG. 8, wherein the served content here presents a video question regarding the patient's health state with elements for text entry.

FIG. 28 is a representation of a display, on the mobile computing device of the patient of FIG. 8, wherein the served content here presents the patient with a video question regarding the patient's health state with an element for text entry. Video player 281 is an area of the display with a featured video question based on the therapeutic regimen optimized for the patient. Text question 282 is a written question posed to the patient with answer element 283 presented to enable the patient to answer the question and present it to the server.

Figure 29:
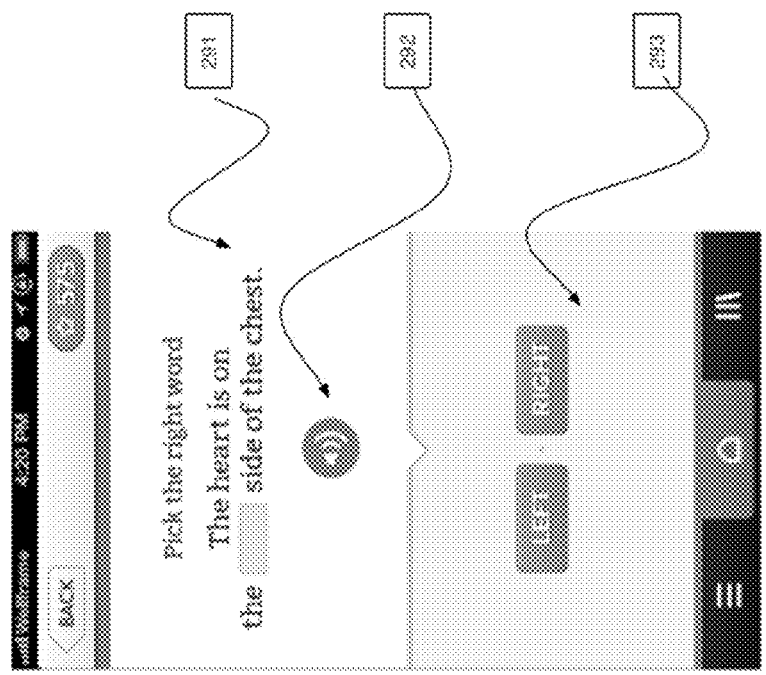
FIG. 29 is a representation of a display, on the mobile computing device of the patient of FIG. 8, wherein the served content here presents a text and audio question with multiple choice answer input.

FIG. 29 is a representation of a display, on the mobile computing device of the patient of FIG. 8, wherein the served content here presents for benefit of the patient a text and audio question with multiple choice answer input. A written question 291 is an area of the display with a featured text question based on the therapeutic regimen optimized for the patient with a missing word. The same question can be presented in audio form to the patient when audio prompt 292 is graphically selected. Answer option 293 is presented to the patient as a prompt to complete the missing word.

Figure 30:
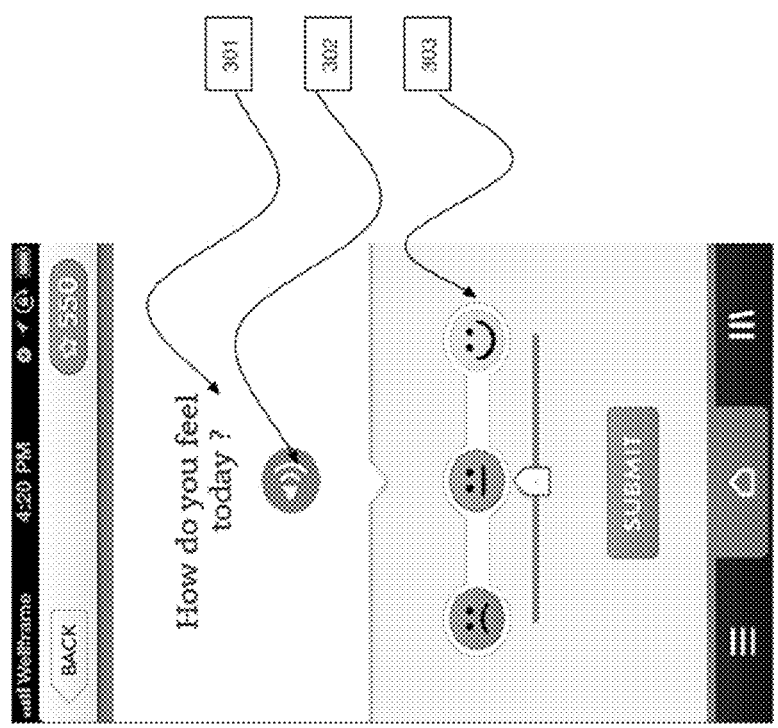
FIG. 30 is a representation of a display, on the mobile computing device of the patient of FIG. 8, wherein the served content here presents a text and audio question with a visual analog scale for answer input.

FIG. 30 is a representation of a display, on the mobile computing device of the patient of FIG. 8, wherein the served content here presents for benefit of the patient a text and audio question with a visual analog scale for answer input. A featured text question 301 based on the therapeutic regimen optimized for the patient with a missing word. The same question can be presented in audio form to the patient when audio prompt 302 is selected. Visual analog scale 303 enables the patient to graphically select an answer based on a visual analog scale.

Figure 31:
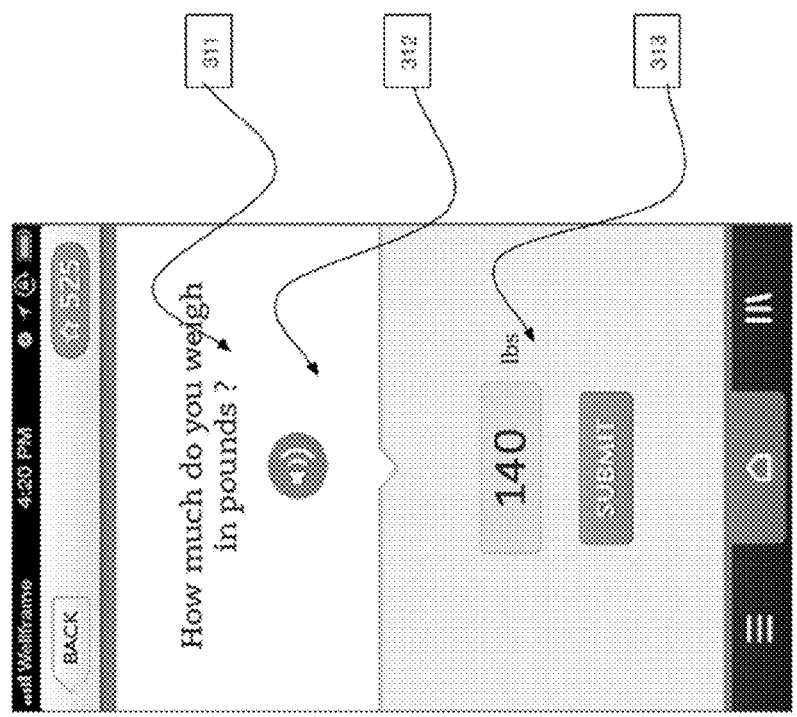
FIG. 31 is a representation of a display, on the mobile computing device of the patient of FIG. 8, wherein the served content here presents a text and audio question with free text answer input.

FIG. 31 is a representation of a display, on the mobile computing device of the patient of FIG. 8, wherein the served content here presents for benefit of the patient a text and audio question with a text and audio question with free text answer input. A written question 311 is an area of the display with a featured text question based on the therapeutic regimen optimized for the patient. The same question can be presented in audio form to the patient when audio prompt 312 is graphically selected. Free text entry box 313 enables the patient to input an alphanumerical answer to the question.

Figure 32:
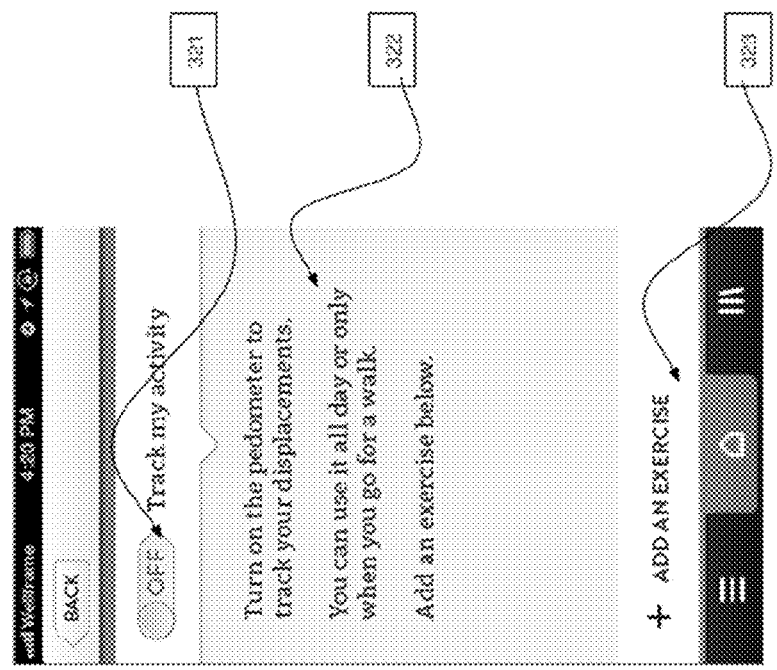
FIG. 32 is a representation of a display, on the mobile computing device of the patient of FIG. 8, wherein the served content here presents a physical activity tracking interface with instructions.

FIG. 32 is a representation of a display, on the mobile computing device of the patient of FIG. 8, wherein the served content here presents for the benefit of the patient a physical activity tracking interface with instructions. At the top of this display is tracking selector 321 which when graphically selected enables the patient to turn on GPS tracking on the dedicated application running on the mobile computing device. User instruction 322 gives written instructions to the user on how to use GPS tracking of their physical activity. Below this is add exercise button 323 which when graphically selected opens a pedometer running on the dedicated application on the patient's mobile computing device.

Figure 33:
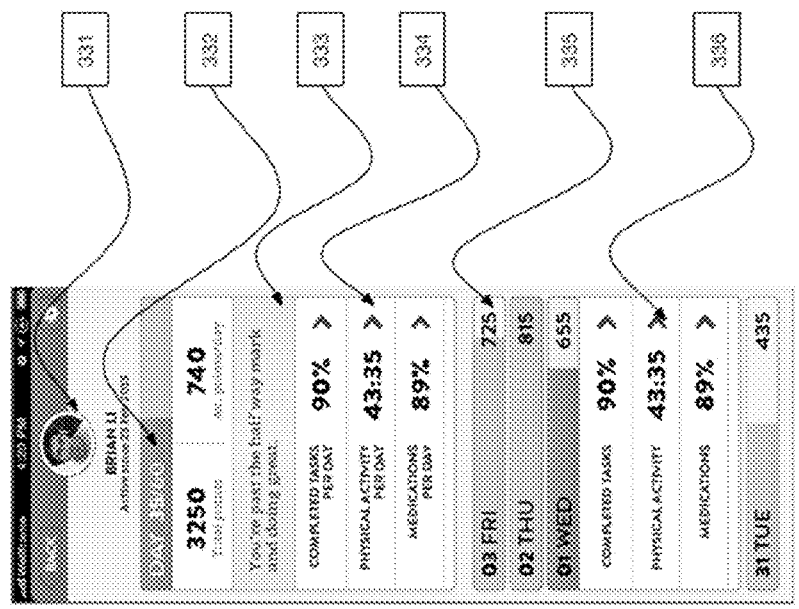
FIG. 33 is a representation of a display, on the mobile computing device of the patient of FIG. 8, wherein the served content here presents a display of summary statistics pertaining to the patient's compliance with the therapeutic regimen.

FIG. 33 is a representation of a display, on the mobile computing device of the patient of FIG. 8, wherein the served content here presents for benefit of the patient a display of summary statistics pertaining to the patient's compliance with the therapeutic regimen. At the top of this display is patient image 331. Below display 331 is progress bar 332 which illustrates the progress of the patient with the regimen customized for the patient. Below progress bar 332 is message 333 intended to give the patient feedback on progress of the patient toward goals of the therapeutic regimen. Below message 333 is a collection of summary statistics 334 featuring numerical feedback to the patient on compliance with the regimen. Below summary statistics 334 is progress bar 335 displaying compliance of the patient on previous days with the regimen. When graphically selected summary statistics for the day in question 336 are served and displayed.

Figure 34:
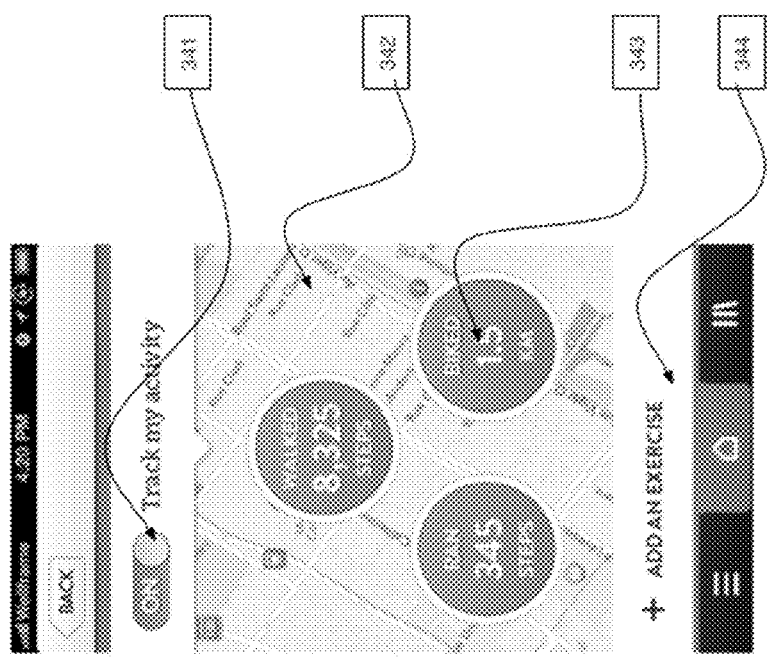
FIG. 34 is a representation of a display, on the mobile computing device of the patient of FIG. 8 and FIG. 32, wherein the served content here presents for benefit of the patient a physical activity tracking interface with summary statistics regarding modalities of activity.

FIG. 34 is a representation of a display, on the mobile computing device of the patient of FIG. 8 and FIG. 32, wherein the served content here presents for benefit of the patient a physical activity tracking interface with summary statistics regarding modalities of activity. At the top of this display is tracking selector 341 which, as previously described as 321, when graphically selected enables the patient to turn on GPS tracking on the dedicated application running on the mobile computing device. Below this is map 342 which displays the patient's current location as determined by GPS. Summary statistics 343 feature summary statistics regarding modalities of the patient's physical activity as served to the mobile computing device. Below this is add exercise button 344 which when graphically selected opens a pedometer running on the dedicated application on the patient's mobile computing device.

Figure 35:
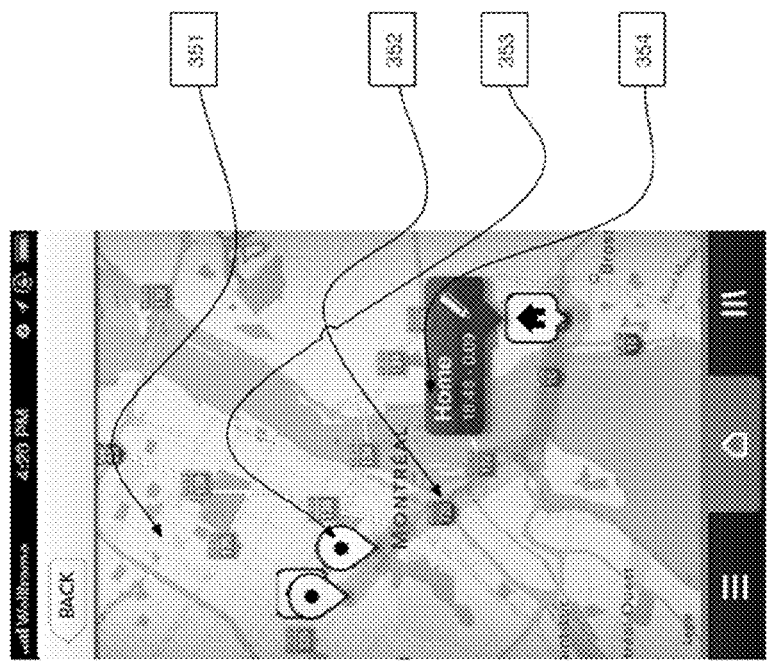
FIG. 35 is a representation of a display, on the mobile computing device of the patient of FIG. 8 and FIG. 32, wherein the served content here presents a geographical rendering of the patient's physical activity over the previous day.

FIG. 35 is a representation of a display, on the mobile computing device of the patient of FIG. 8, FIG. 32 and FIG. 34; wherein the served content here presents for benefit of the patient a geographical rendering of the patient's physical activity over the previous day. At the top of this display is map 351 upon which is overlaid path 352 which displays the patient's movement as tracked by the GPS sensor running on the mobile computing device. On top of this are overlaid waypoints for navigation 353. Below this is dialog box 354 which displays the nature of the patient's current location as entered by the patient.

Figure 36:
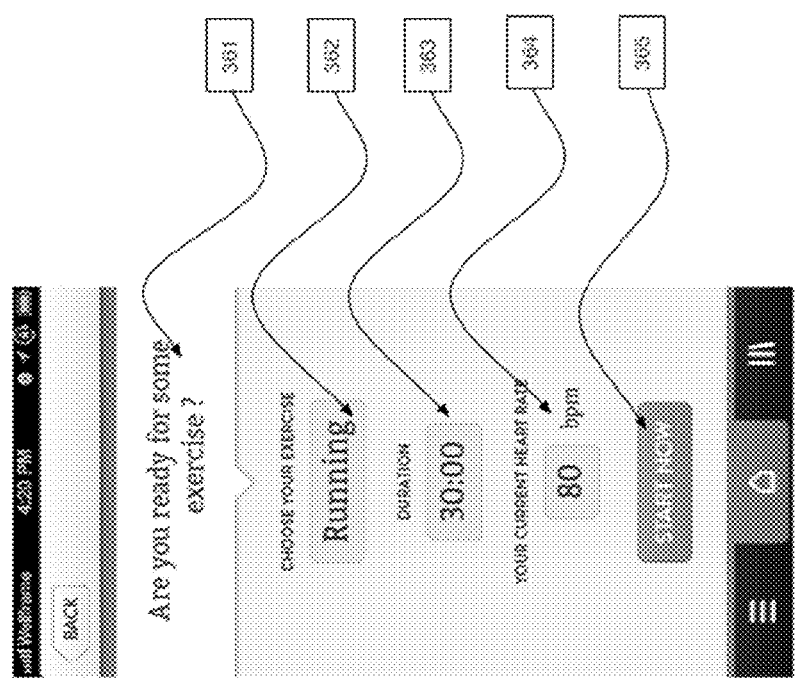
FIG. 36 is a representation of a display, on the mobile computing device of the patient of FIG. 8, FIG. 32 and FIG. 34; wherein the served content here presents for benefit of the patient a manual activity tracking interface.

FIG. 36 is a representation of a display, on the mobile computing device of the patient of FIG. 8, FIG. 32 and FIG. 34; wherein the served content here presents for benefit of the patient a manual activity tracking interface. At the top of the display is text question 361, below this is physical activity entry element 362 which enables the patient to select the type of physical activity to manually track. Below this is time entry element 363 which enables the patient to select the duration of the prospective physical activity that they would like to manually track. Below this is heart rate entry element 364 which enables a patient to enter the patient's heart rate either manually, through the sensors on the mobile computing device or through connection to an external device. At the bottom of the display is start button 365 which turns on the pedometer as described in FIG. 37 and FIG. 38.

Figure 37:
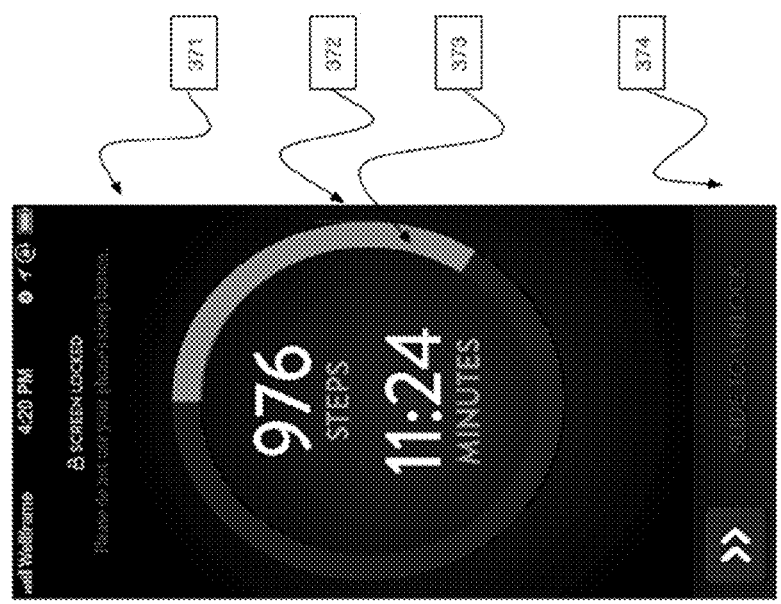
FIG. 37 is a representation of a display, on the mobile computing device of the patient of FIG. 8, FIG. 32 and FIG. 36, wherein the served content here presents a pedometer in it's active state with steps taken and time completed.

FIG. 37 is a representation of a display, on the mobile computing device of the patient of FIG. 8, FIG. 32 and FIG. 36, wherein the served content here presents a pedometer in it's active state with steps taken and time completed. This pedometer operates within the application running on the patient's mobile computing device to track the patient's movement using data from the accelerometers on the mobile computing device. At the top of this display is notification 371 which informs the patient that the screen is locked to avoid accidental graphical interaction with the display whilst the mobile computing device is in the patient's pocket. Below this is step tracking element 372 which shows how many steps the patient has taken and in what time with a graphical element 373 displaying the proportion of the activity target that is complete. Below this on the display is the unlock slider 374 which when graphically selected disables the locked screen and enables the patient to graphically interact with the display on the device as detailed in FIG. 38.

Figure 38:
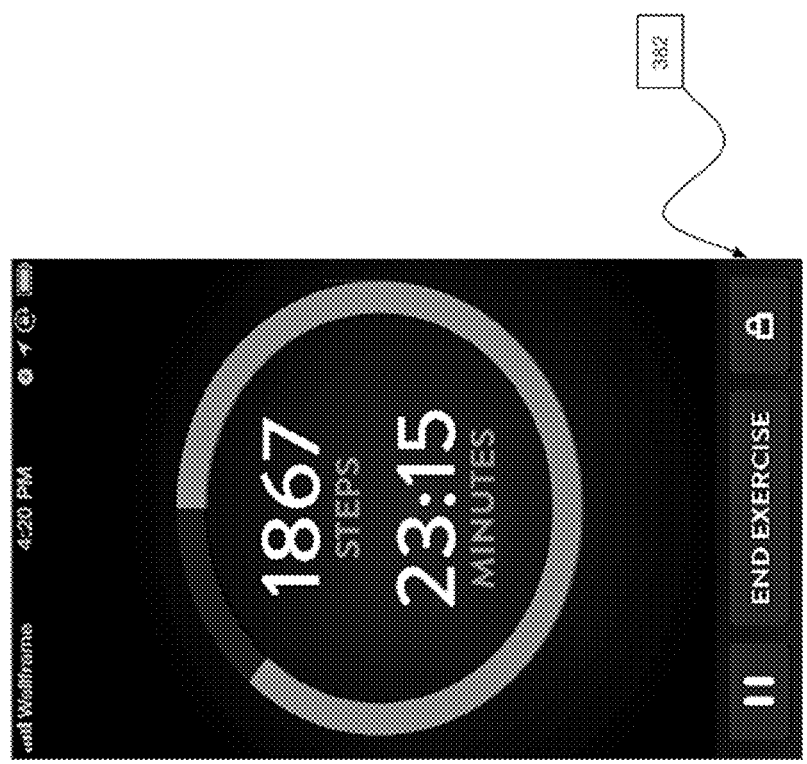
FIG. 38 is a representation of a display, on the mobile computing device of the patient of FIG. 8, FIG. 32, FIG. 36 and FIG. 37, wherein the served content here presents a pedometer in its inactive state.

FIG. 38 is a representation of a display, on the mobile computing device of the patient of FIG. 8, FIG. 32, FIG. 36 and FIG. 37, wherein the served content here presents a pedometer in its inactive state. Buttons in interaction area 382 enable a patient to end the session of physical activity and return to FIG. 8 or to lock the screen, continue with tracking activity and return to FIG. 37.

Figure 39:
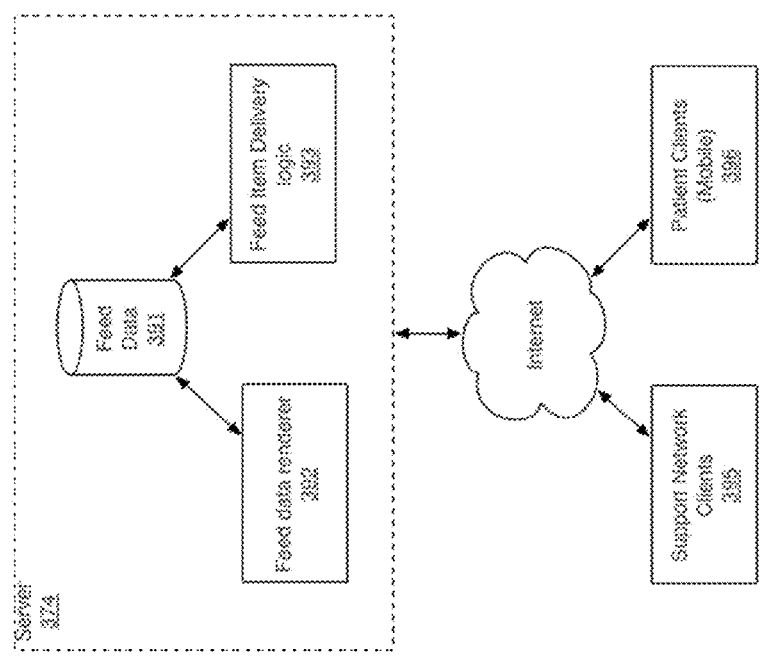
FIG. 39 is a block diagram of system architecture for an exemplary embodiment of a computerized method of facilitating communication and interaction between patients and their support networks (other patients, family members, health practitioners, etc) via the application running on a patient's mobile computing device and the computer system of persons involved in the patient's support network.

FIG. 39 is a block diagram of system architecture for an exemplary embodiment of a computerized method of facilitating communication and interaction between patients and their support networks (other patients, family members, health professionals, etc), in this embodiment called a "feed", via the application running on a patient's mobile computing device and the computer system of persons involved in the patient's support network. The server 392 stores feed data 391 which is a set of items representing a narrative report of patient activities including interactions with health professionals, specific actions by the patient relative to the regimen, and interactions with individuals in the patient's support network. The server implements logic for retrieving and rendering a set of such items from the feed data 391. Logic for determining which individuals in the patient's support network should see the given set of feed items, shown in FIG. 39 as Feed Item Delivery Logic 393, is implemented by the server to choose individuals in the patient's support network to whom the server transmits, over the internet to the computer systems of the selected individuals in the patient's support network, the selected set of feed items. The server causes presentation of the selected feed items to the clients of individuals in the patient's social network 395, as determined by the Feed Item Delivery Logic 393, and to the patient via the application running on such patient's mobile computing device 396.

Figure 40:
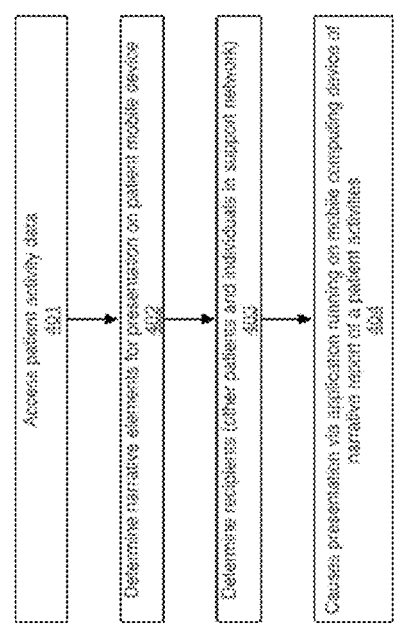
FIG. 40 is a block diagram illustrating logical flow of the embodiment of FIG. 39.

FIG. 40 is a block diagram illustrating logical flow of the embodiment of FIG. 39. The server accesses patient activity data 401, also referred to as feed data 391 in FIG. 39. Next the server determines the appropriate narrative elements, from the patient activity data 401, for presentation 402 to the patient via the application running on the patient's mobile computing device and for presentation to individuals in the patient's support network via the application running on the individual's computer system. The server then determines the recipients of such items 403, which may include the patient all individuals in the patient's support network, and then causes presentation of such narrative elements to the patient via the application running on the patient's mobile computing device and to the individuals determined in the support network 403 via the application running on their computer systems 404.

Figure 41:
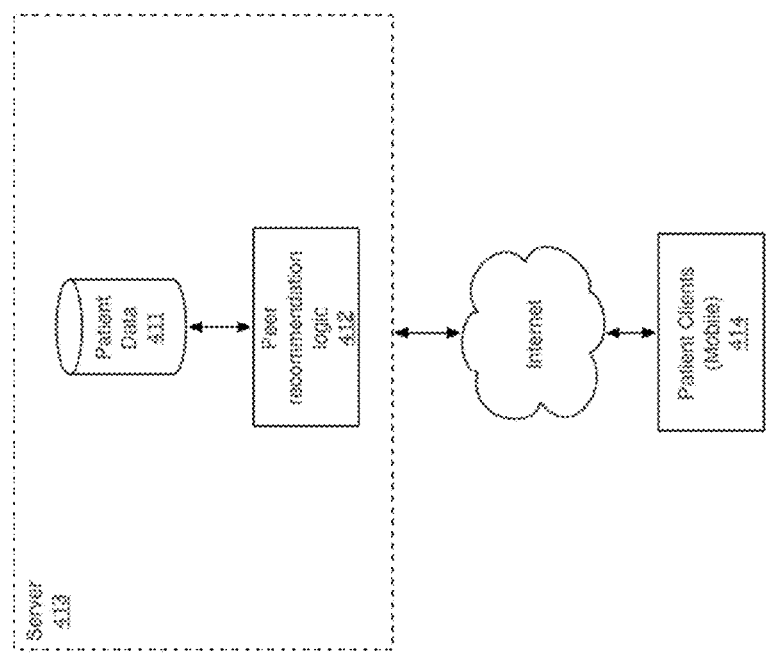
FIG. 41 is a block diagram of system architecture for an embodiment of a peer-to-peer (patient-to-patient) recommendation engine for expanding a patient's support network in order to help improve the patient's compliance with a therapeutic regimen.

FIG. 41 is a block diagram of system architecture for an embodiment of a peer-to-peer (patient-to-patient) recommendation engine for enhancing a patient's support network in order to help improve the patient's compliance with a therapeutic regimen. A server 413 handles communication over the internet with mobile computing devices of patients which are here collectively shown as item 414 in FIG. 41.

Stored patient data 411 (such as patient gender, age, medical condition, compliance with the patient's therapeutic regimen, etc) is accessed by the peer recommendation logic 412, in order to match a particular patient to a set of other patients based on some measure of similarity determined by such logic 412 operating on the patient data 411, and returns a set of such similar patients. For example, a patient of a particular age, gender, medical condition, and location may be matched with other patients of the same gender, medical condition, age, and location. The server 413 causes transmission of a message introducing a member of the identified set to the given patient.

Figure 42:
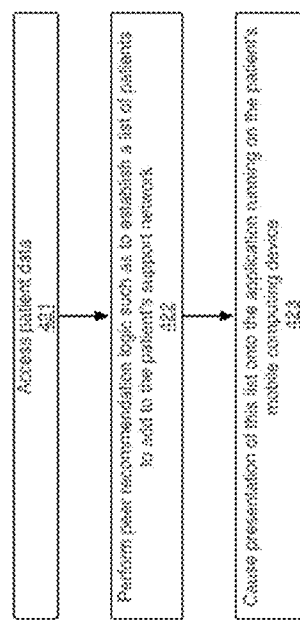
FIG. 42 is a block diagram illustrating logical flow of the embodiment of FIG. 41.

FIG. 42 is a block diagram illustrating logical flow of the embodiment of FIG. 41. Here, the server accesses patient data in process 421 for a particular patient and then in process 422 performs logic on such data, seen in FIG. 42 as the peer recommendation logic 412, which determines a set of similar patients (consisting of other patients also stored in the patient database) to add to the given patient's support network in order to help improve the given patient's compliance with the therapeutic regimen. In process 423, the server causes presentation of such identified set onto the application running on the patient's mobile computing device by causing transmission of a message introducing members of the identified set to the given patient.

Figure 43:
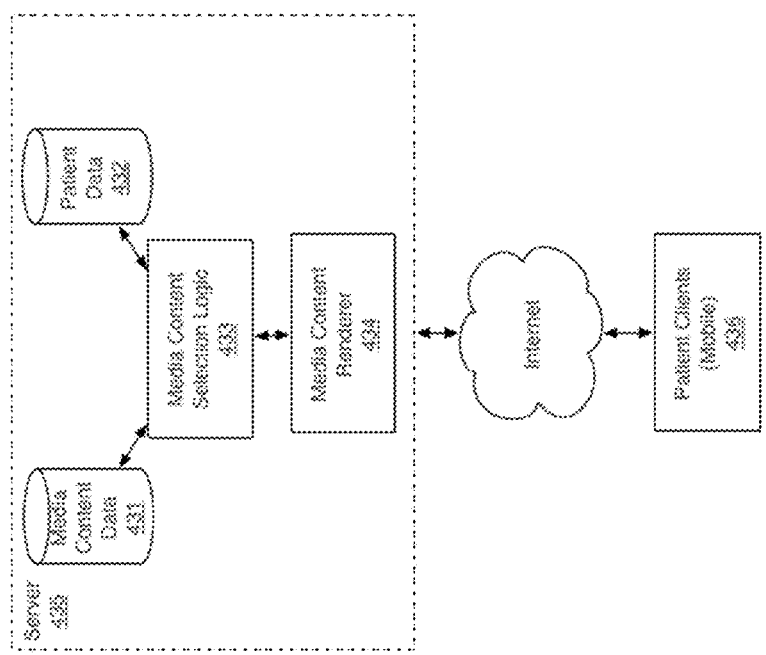
FIG. 43 is a block diagram of system architecture describing an embodiment of computerized selection and presentation to the application running on a patient's mobile computing device of media content selected to assist the patient in achieving goals of the therapeutic regimen.

FIG. 43 is a block diagram of system architecture describing an embodiment of computerized selection and presentation to the application running on a patient's mobile computing device of media content selected to assist the patient in achieving goals of the therapeutic regimen. The server 435 stores both media content data 431 and patient data 432. The server 435 contains logic, seen in FIG. 43 as media content selection logic 433, which given patient data 432, selects a set of media content from the media content data 431 that is determined to assist a patient in achieving goals of the therapeutic regimen. For example, the server 435 may select content that matches the given patient's specific medical condition or matches a patient's physiological data. In a specific embodiment of this invention, this matching may be made by tagging media content with keywords and matching the keywords to the retrieved patient data. The server contains logic, referred to in FIG. 43 as media content renderer 434, to render the selected media content in a user-friendly manner and cause presentation of such set onto the application running on such patient's mobile computing device 436.

Figure 44:
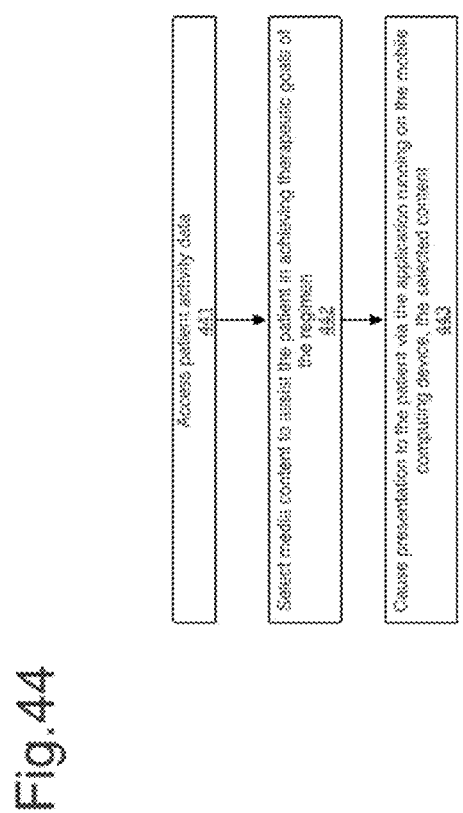
FIG. 44 is a block diagram illustrating logical flow of the embodiment of FIG. 43.

FIG. 44 is a block diagram illustrating logical flow of the embodiment of FIG. 43. In FIG. 44, the server accesses stored patient data in process 441 for a particular patient which is used by the server's logic to select a set of media content in process 442 to assist the patient in achieving goals of the therapeutic regimen. The server causes presentation, in process 443, of the selected set of media content to the patient via the application running on the mobile computing device of such patient.

Figure 45:
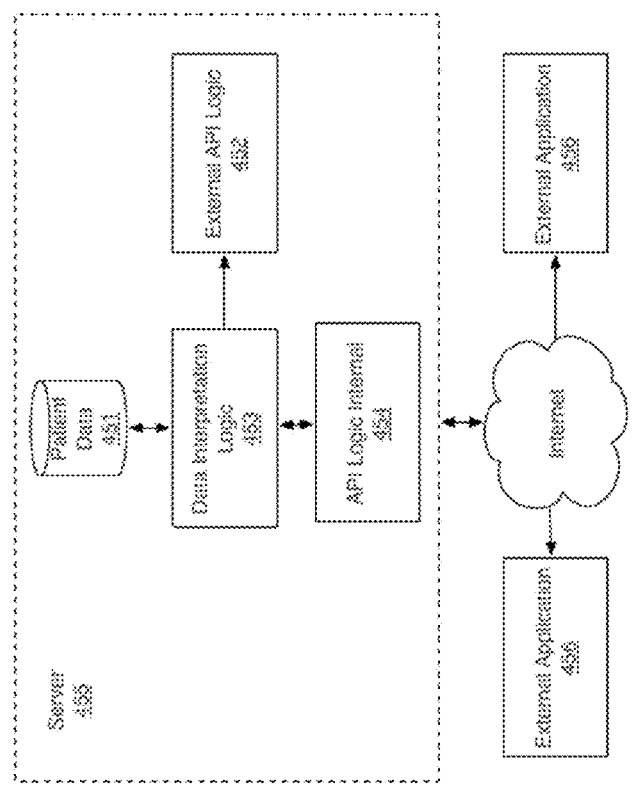
FIG. 45 is a block diagram of system architecture describing a computerized system for connecting and extracting relevant patient data from external devices, software, and other data sources.

FIG. 45 is a block diagram of system architecture describing an embodiment of a computerized system for connecting to and extracting relevant patient data from external applications. As can be seen in FIG. 45, a server 455 handles patient data 451 stored in a database. In this embodiment, the server 455 also contains logic to interface with external applications, depicted in FIG. 45 as External API Logic 452, in order to collect physiological and pathological data for a patient not readily available through the patient's interaction with the application running on the patient's mobile computing device. External data sources include but are not limited to wireless weight scales, wireless heart rate monitors, external applications for tracking physical activity, external applications for tracking medication compliance, etc. In addition, the server contains logic for external applications, shown collectively in FIG. 45 as External Application 456, to interface directly with the server, seen in FIG. 45 as API Logic Internal 454. The server contains logic, seen in FIG. 45 as Data Interpretation Logic 453, which consolidates, into a common data format, data from API logic internal 454 and External API Logic 452, to be stored as patient data 451. An embodiment of this system could, for example, determine a fixed set of database columns, also referred to as the database schema, into which the server's data interpretation logic 453 stores data from the External API Logic 452 and API Logic Internal 454.

Figure 46:
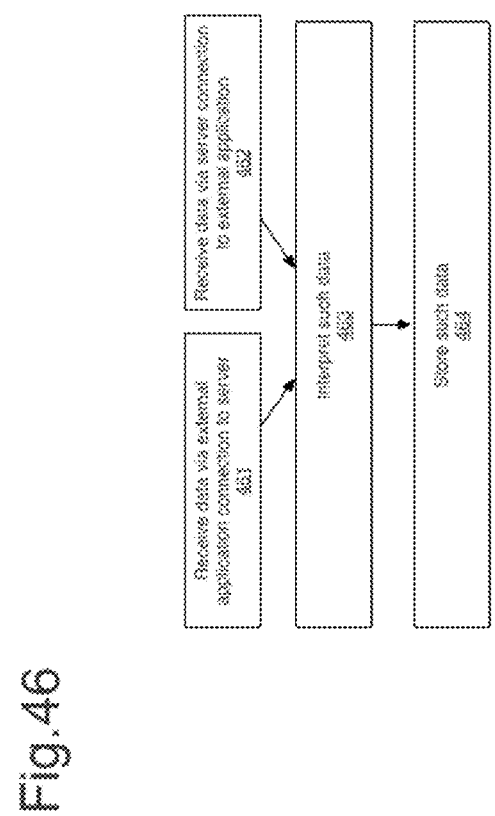
FIG. 46 is a block diagram illustrating logical flow of the embodiment of FIG. 45.

FIG. 46 is a block diagram illustrating logical flow of the embodiment of FIG. 45. In FIG. 46, the server receives patient physiological and pathological data in process 461 via external application connection to the server and receives data via the server's connection to external applications in process 462. The server interprets and consolidates into a common format the data received from both of these sources in process 463 then stores this new patient data in a database in process 464.

Figure 47:
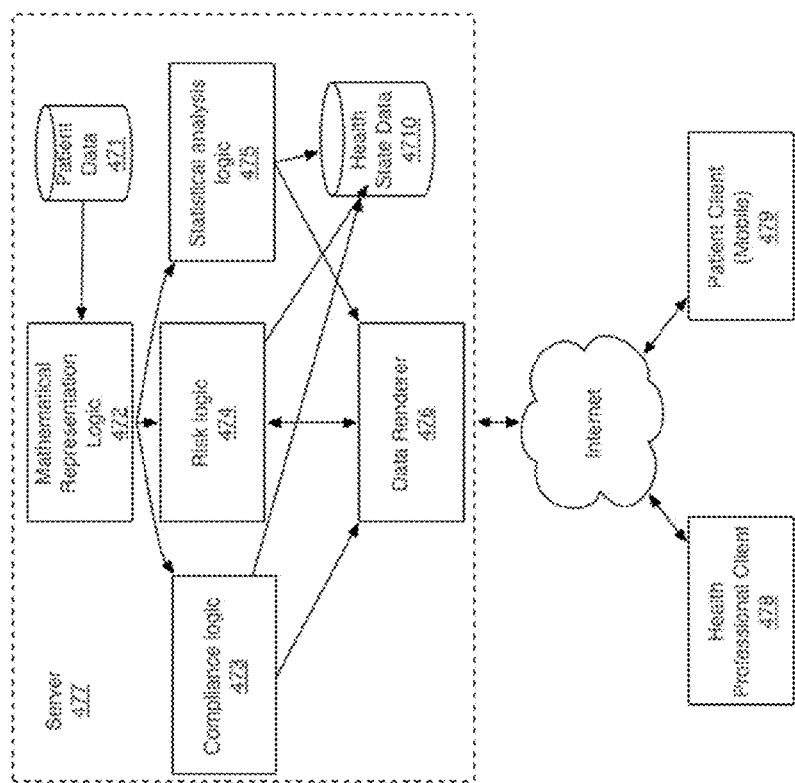
FIG. 47 is a block diagram of system architecture for representing patient data in a mathematical format, performing analytics on the data, and causing presentation onto a health practitioner's computer system and the application running on a patient's mobile computing device.

FIG. 47 is a block diagram of system architecture for representing patient data in a mathematical format, performing analytics on the data, determining patient and population health state, and causing presentation of such data and analytics onto a health professional's computer system and the application running on a patient's mobile computing device. In FIG. 47 the server 477 accesses stored physiological and pathological patient data 471. The server uses such data in its logic, seen in FIG. 47 as Mathematical Representation Logic 472, to convert the stored patient data 471 into a mathematical representation. Several possible embodiments of mathematical representation of such data exist, some examples including vector space models of different patient attributes, network models of patient attributes, Bayesian or probabilistic models of patient attributes, time series models of patient attributes, entropy and information-based models of natural language and free-form text entries, etc. The server uses such representation derived from the Mathematical Representation Logic 472 to compute different types of patient level and population level analytics to derive and classify patient and population health state. Exemplary embodiments of the server's logic, seen in FIG. 47, for such analytics include compliance logic 473, risk logic 474, and statistical analysis logic 475. An exemplary embodiment of the result of compliance logic is a discrete value representing a patient's compliance with the regimen, which may be represented by a percentage of to-do list items completed in a period of time, or changes in the patient's physiological or pathological values or goals of the therapeutic regimen achieved to date, or a function of these values in combination. An exemplary embodiment of the result of risk logic is a discrete value representing the patient's non-compliance with the regimen which may be represented by a percentage of to-do list items not completed, or changes in the patient's physiological or pathological values or goals of the therapeutic regimen not achieved to date. Several methods of implementing the server's compliance logic 473 and risk logic 474 exist, an example being time-based weighted averages of patient tasks completed. Statistical analysis logic 475 can be carried out by several methods, examples including parametric and non-parametric analysis methods, Bayesian analysis methods, or machine learning techniques, such as neural networks and support vector machines for statistical patient classification, based on patient physiological and pathological data and patient tasks completed, all accessed via the patient database 471. The derived patient health states are stored, by the server, in the health state database 4710. The server also contains logic, shown in FIG. 47 as Data Renderer 476, to render the results of the different types of analytics in a human-readable format, examples being graphs, tables, and charts. The server causes presentation of such results from the Data Renderer 476 to the health professional clients, collectively shown as health professional Client 478 in FIG. 47, and to the application running on patients' mobile computing device, collectively shown as Patient Client 479 in FIG. 47.

Figure 48:
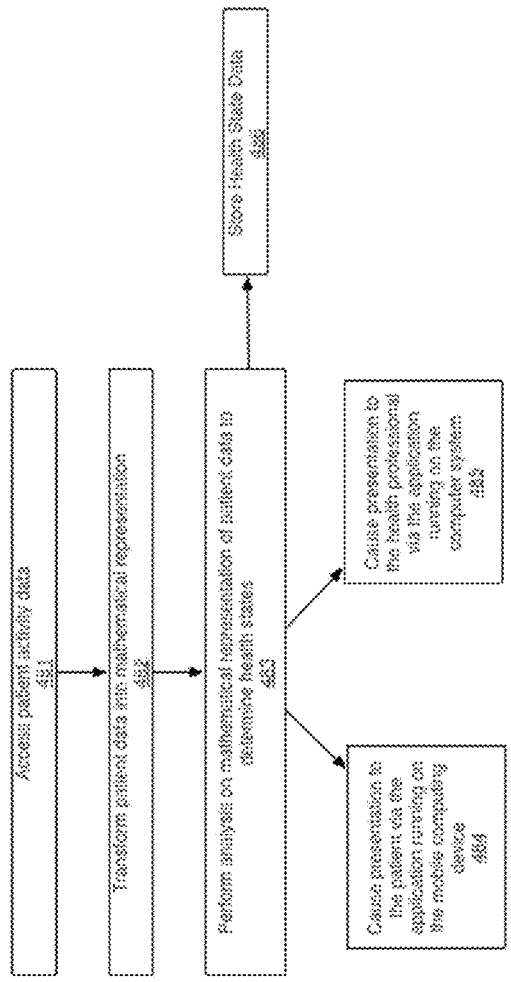
FIG. 48 is a block diagram illustrating logical flow of the embodiment of FIG. 47.

FIG. 48 is a block diagram illustrating logical flow of the embodiment of FIG. 47. In process 481, the server accesses patient data from a database. Using such data, in process 482, the server transforms the data into a mathematical representation, on which the server performs analytics (in process 483) such as patient compliance analysis, patient risk analysis, and statistical analysis and determines patient health states. The server stores such health state data in process 486. The server causes presentation of the results of the performed analysis to the patient via the application running on the patient's mobile computing device (in process 484) and to the appropriate health professionals via the application running on the health professional's computer system (in process 485).

Figure 49:
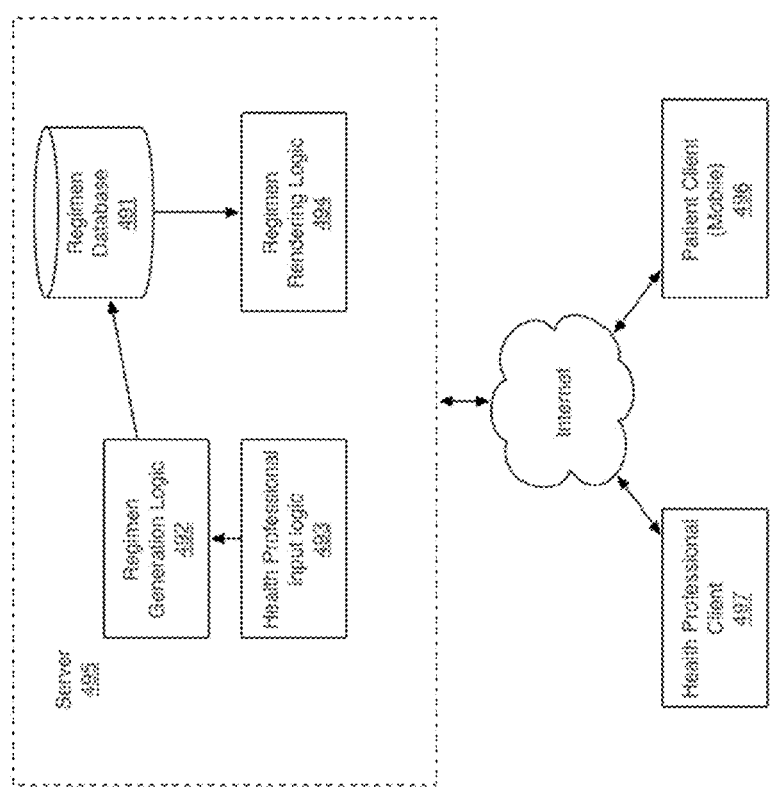
FIG. 49 is a block diagram of system architecture for a computer-implemented method of developing and causing presentation of a therapeutic regimen to be delivered to patients through the application running on a patient's mobile computing device

FIG. 49 is a block diagram of system architecture for a computer-implemented method of developing and causing presentation of a therapeutic regimen to be delivered to patients through the application running on a patient's mobile computing device. A server 495 contains logic to process health professional input which, in an embodiment of the invention specifies the goals of the therapeutic regimen, and the medical condition related to the therapeutic regimen, shown in FIG. 49 as health professional input logic 493, via an application on the health professional's computer system. The server contains further logic, shown in FIG. 49 as Regimen generation logic 492, to automatically generate a therapeutic regimen based on the goals of the therapeutic regimen specified by the health professional via an application on the health professional's computer system, shown as Health Professional Client 497 in FIG. 49, and processed by the server via its health professional input logic 493. The server stores therapeutic regimens, generated by the server's regimen generation logic 492, in the regimen database 491. Such regimen data is accessed by logic operative to rendering the retrieved therapeutic regimen as a list of at least daily "to-do" items, seen as the Regimen Rendering Logic 494 in FIG. 49. The server causes presentation of such list of "to-do" items to the patient via the application running on the patient's mobile computing device 496.

Figure 50:
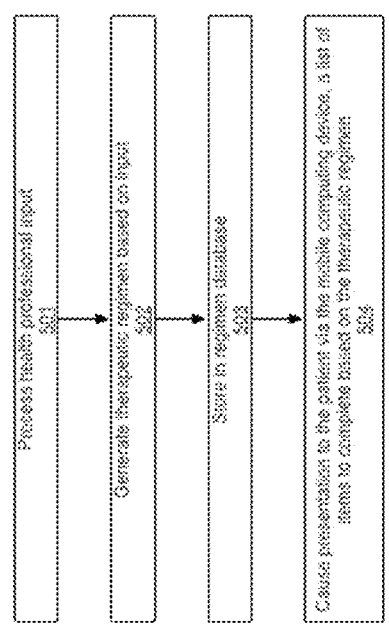
FIG. 50 is a block diagram illustrating logical flow of the embodiment of FIG. 49.

FIG. 50 is a block diagram illustrating logical flow of the embodiment of FIG. 49. The server processes the health professional's input containing goals of the therapeutic regimen in process 501, and generates a therapeutic regimen based on such goals in process 502. The server stores the generated therapeutic in the regimen database in process 503. Such data is accessed by the server in order to cause presentation to the patient in process 504 via the mobile computing device, a list of "to-do" items to complete based on the therapeutic regimen.

Figure 51:
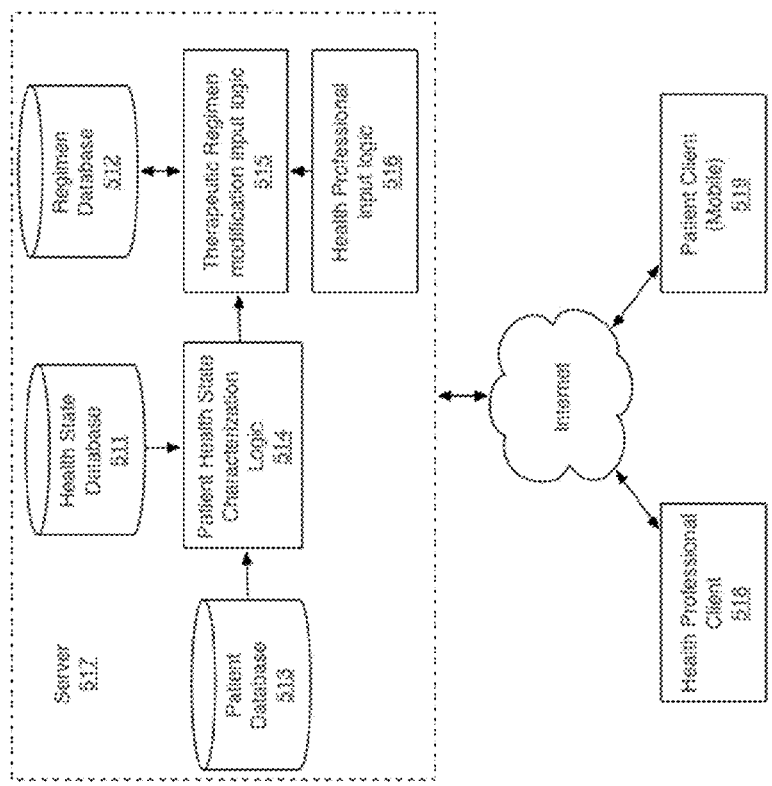
FIG. 51 is a block diagram of system architecture for a computer-implemented method of customizing a retrieved therapeutic regimen based on the specific physiological and pathological parameter values applicable to the current medical condition of a given patient, and based on health practitioner input via a user interface, presented on the health practitioner's computer system, with a view to improving such patient's progress toward goals of the therapeutic regimen.

FIG. 51 is a block diagram of system architecture for a computer-implemented method of customizing a retrieved therapeutic regimen based on the specific physiological and pathological parameter values applicable to the current medical condition of a given patient, and based on health professional input via a user interface, presented on the health professional's computer system, with a view to improving such patient's progress toward goals of the therapeutic regimen. The server 517 stores patient physiological and pathological data in the patient database 513, stores health state data in the health state database 511, and stores regimen data in the regimen database 512. The patient data 513 and health state data 511 are accessed by logic operative in determining the health state of a particular patient given the physiological and pathological parameter values of such patient, such logic shown as Patient Health State Characterization logic 514 in FIG. 51. Such patient health state is determined by the Patient Health State Characterization logic 514, the result of logic to modify the patient's goals of the therapeutic regimen as specified by a healthcare professional via the application running on such healthcare professional's computer system 518, shown in FIG. 51 as Health Professional input logic 516, and the patient's current therapeutic regimen, stored in the regimen database 512, are accessed by logic operative in modifying and customizing the patient's therapeutic regimen, shown in FIG. 51 as Therapeutic Regimen modification input logic 515. The server causes presentation of the modified therapeutic regimen to the patient via the application running on the patient's mobile computing device and to the appropriate health professional via the application running on the health professional's computer system.

Figure 52:
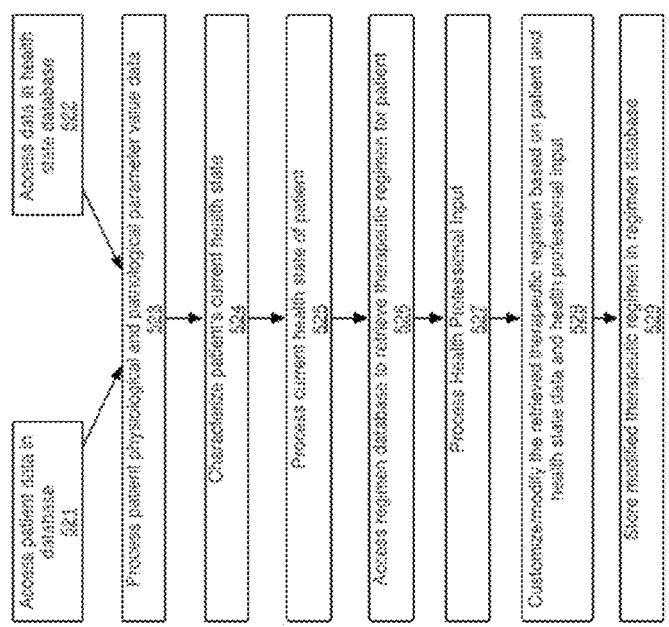
FIG. 52 is a block diagram illustrating logical flow of the embodiment of FIG. 51.

FIG. 52 is a block diagram illustrating logical flow of the embodiment of FIG. 51. The server accesses patient data in a database process 521 and health state data in a database in process 522. The server processes the patient's physiological and pathological parameter value data in process 523 and uses the results to characterize the patient's current health state in process 524. The server further processes such health state of the patient in process 525 and accesses the regimen database to retrieve the therapeutic regimen for the patient in process 526. The server also processes input of the health professional, specifying modified goals of the therapeutic regimen for the patient in process 527, and modifies the retrieved therapeutic regimen for the patient, based on the accessed patient data, health state data, and health professional input in order to assist the patient in achieving the new goals of the therapeutic regimen. The modified therapeutic regimen is stored in the regimen database.

Use Case for the Apparatus and Method for Improving Compliance with a Therapeutic Regimen: Chronic Disease Management.

In one embodiment, the invention herein is implemented using a dedicated application running on a mobile computing device of each patient, a set of servers, a set of databases and a web based dashboard that together improve a patient's compliance with the patient's therapeutic regimen by presenting the regimen as a daily to-do list and collecting information in order to optimize the future regimen in response to patient's interaction with the past regimen to achieve the maximum likelihood of the patient's reaching the patient's goals of the therapeutic regimen. The effect of this approach across a population of patients is improved compliance to therapeutic regimens optimized according to individual patient needs and improved population health outcomes.

A patient with a chronic disease affecting their physical health such as Ischemic Heart Disease (Heart Attack and Angina), Diabetes, Heart Failure, Cancer or Chronic Obstructive Pulmonary Disease or a chronic disease affecting their mental health such as depression, bipolar affective disorder or schizophrenia; when admitted to the hospital or seen by a health professional in an office setting for an episode of planned or emergency care is discharged with a set of verbal (hurried instructions in the clinic or on discharge from the hospital) and/or written instructions (a thick booklet of printed sheets) on how to manage their disease and engage with the health system to prevent a relapse or deterioration and ensure an optimal future health state.

In some instances the patient may be supported at home by a nurse, health coach, care manager, a dedicated rehabilitation facility or their own primary care physician. Such programs of continuing care exist to reduce readmissions due to foreseeable or unforeseeable consequences of the index medical condition and to address the risk factors for a repeat event occurring. These programs tend to involve a patient visiting a health professional, a health professional visiting a patient or a phone interaction between the patient and health professional.

The existing programs are all complicated for patients and/or have difficulty in engaging and retaining enough people for long enough to have a meaningful population health impact. Tele-medicine solutions have been developed to improve the efficiency of care delivery in the home but tele-medicine solutions to be costly (as they require dedicated hardware), are difficult for patients to use, are not portable, and are designed primarily for information collection rather than information dissemination and patient engagement and do not involve the patient's family and support network in the care of the patient.

The embodiment of described in this use case is initially optimized for the aforementioned medical conditions but is designed in such a way that the same functionality, design and engagement principles are tractable to any disease: sudden onset or long term onset and in the hospital, clinic or community setting.

A specific use case for the this embodiment is for a patient who has had a heart attack and is admitted to a hospital for treatment. Patient in this category are already using the dedicated application after discharge from hospital to promote recovery from heart disease as part of a pilot deployment in Massachusetts. In this pilot deployment, a patient is guided by a clinician to install the application during the process of discharge from the hospital. If they do not have a device the patient is lent a device with the application loaded. The application guides the patient through what they need to do to ensure they are compliant with a recommended care regimen and enables two-way communication between the patient, their care network (their family and friends) and the health professionals involved in their care (in the hospital and in other external clinics.)

Once the patient has installed the application, they receive a dynamically generated daily to-do list with a set of to-do items that they are able to complete on the dedicated application running on the patient's mobile computing device. The to-do items include but are not limited to written education material, video education items, animated education items, questions, prompts to use the GPS and/or accelerometer sensors on the mobile computing device to track physical activity, prompts to photograph or video record health behavior, prompts to capture data using a connected device and custom messages from a health professional. A patient can perform each of these items in turn or in any desired sequence from the patient's device and each interaction with the application and hence with the patient's therapeutic regimen is recorded on the server.

Rules can be established such that a patient who is not completing any to-do list items or is completing less to-do list items than ideal or doing more than ideal can be identified for follow up as described earlier. The conditions under which follow up is required and what kind of follow up is required can be predefined and as such for the majority of cases, care can be managed by the system with human intervention to make the patient feel like someone is reviewing their progress and in particular to manage cases who most need human input.

Patients who want to explore a thematic area relevant to their regimen in greater depth can access a library view on the application running on a mobile computing device. The library features written and video content and also content from external web sources that are stored on the server and rendered to the mobile device.

A patient often has their own care network (family and friends) who are motivated to help the patient, involvement of the care network is known to be associated with improved compliance with a therapeutic regimen but who are often excluded from existing care delivery methods and from most tele-medicine solutions. Within the dedicated application running on a mobile computing device there is a private social network to enable communication between a patient and their care network. Based on privacy permissions as granted by the patient, every action performed the patient as part of the patient's regimen can be served to a feed. A care provider, a family member, a friend or another patient can then interact with the feed to support the patient in compliance with the regimen.

A companion mobile application is available for members of a patient's care network (family and friends) where the members of a care network can receive the same or complementary to-do list items as the patient and have access to the library and the social feed to monitor and encourage the patient's compliance with the regimen.

pathological and compliance data as described in [00121] and as a result of a health state the server executes the actions below.

Further modifications of the regimens can be made according to patient subgroup where a subgroup is a set of patients with common health state who require common customizations in a regimen, for example: diabetics, the elderly, women, smokers, people with substance misuse problems and people with multiple co-morbidities.

In the table below acute refers to a sudden change in health state, typically in the space of one day and chronic refers to a longer-term persistence of a health state, typically for one week.

| Health state variant | Health state sub-variant | Regimen changes |
|---|---|---|
| Optimal | Acute | Maintenance. Encouragement. |
| | Chronic | Health professional review of follow up schedule. Health Professional Contact. |
| Sub-Optimal | Acute | Trial of system modified regimen. |
| | Chronic | Health professional review of appropriateness of regimen. Health Professional Contact. |
| Non Adherent | Acute | Trial of system modified regimen. |
| | Chronic | Health professional review |
| Ineligible | Cure | Health professional review |
| | Deceased | Health professional review |
| | Transition | Health professional review |

The embodiments of the invention described above are intended to be merely exemplary; numerous variations and modifications will be apparent to those skilled in the art. All Health States and associated regimens. Example of Myocardial Infarction (MI)

| Health state | Typical Venue of care | Associated Physiology | Associated Pathology | Regimen | Therapeutic Goals of Regimen |
|---|---|---|---|---|---|
| At risk (with symptoms or without symptoms) | Outpatient | High BP High Cholesterol High Blood Sugar Reduced Vascular Compliance | Atheromatous Vascular Disease | Primary Prevention Regimen Cardiovascular disease | Control of risk factors and prevention of Angina and Ischaemic Heart Disease. |
| Index Event (Acute MI) | Inpatient | Acute Myocardial Infarction | Myocardial Ischaemia, necrosis and re-modelling | Acute Secondary Prevention Myocardial Infarction. | Reversal or management of acute vascular occlusion. |
| Rehabilitation | Outpatient | Altered Coagulation status Elevated Blood Pressure Transition to Controlled BP, Cholesterol, Blood Sugar, Clotting status | Myocardial Re-modelling and new blood vessel formation. | Chronic Secondary Prevention Myocardial Infarction. | Prevention of repeat Myocardial Infarction. Return to pre-morbid functioning. Early detection of known complications. |
| Secondary Complications: Heart Failure (new index event) | Outpatient or Inpatient | Low Oxygen Saturation Low BP Raised Jugular Venous Pressure Reduced Ventricular Ejection Fraction | Left Ventricular Failure, Diastolic dysfunction. Arrhythmia, Cardiomyopathy Cardiac Fibrosis Renal Failure | Secondary Prevention of Heart Failure | Maintenance of functioning Avoidance of deterioration. Early detection of decompensation |

Health State Variants, Sub-Variants and Regimen Changes

Each of the states listed in the table associated with 0 have variants and sub-variants as listed below. The server computationally defines health states according to physiological, such variations and modifications are intended to be within the scope of the present invention as defined in any appended claims.

What is claimed is:

1. A computer-implemented method for providing dynamically customized regimens to a patient population and real-time monitoring of population member compliance with such regimens in a system having a server in communication with a plurality of wirelessly-connected internet-coupled patient mobile computing devices over a first network that includes the internet and further in communication with a health practitioner computer system over a second network that includes the internet, each of the patient mobile computing devices associated with a given patient and running a patient client application, the method comprising:

(A) for each patient:
  (i) receiving and storing at the server physiological data pertinent to such patient;
  (ii) receiving and storing at the server data characterizing a therapeutic regimen for such patient; and
  (iii) iteratively:
  (a) customizing, using processes of therapeutic regimen modification input logic of the server, the therapeutic regimen for such patient based on the physiological data pertinent to a medical condition of such patient and patient compliance data and patient-reported data;
  (b) dynamically generating, by the server, on at least a daily basis, an updated list of items from the customized therapeutic regimen to be performed by the patient;
  (c) transmitting, by the server to the patient mobile computing device, via an internet-coupled access device used to establish a wireless connection to the patient mobile computing device, the dynamically-generated updated list of items to be performed by the patient, such transmission activating the patient client application running on the patient mobile computing device to display (i) the updated list of items from the customized therapeutic regimen to be performed by the patient on the date of presentation of the updated list and (ii) a region, on a display of the mobile computing device, that enables completion of items on the updated list using the patient client application running on the mobile computing device and that causes sending by the mobile computing device to the server of patient compliance data, patient-reported data, and physiological data so that each interaction with the patient's customized therapeutic regimen using the patient client application is dynamically recorded on the server in real time;
  (d) receiving at the server from the mobile computing device the patient compliance data, the patient-reported data, and the physiological data, and storing the compliance data, the patient-reported data, and the physiological data;
  (e) using the compliance data, the patient-reported data, and the physiological data (i) in determining a time-based weighted average of patient tasks complete to calculate a quantity corresponding to an extent of compliance of such patient with goals of the therapeutic regimen customized for such patient and (ii) in generating the dynamically updated list for presentation to the patient via the mobile computing device on a subsequent occasion; and
  (f) storing the quantity and the updated list;
(B) retrieving by the server, for each patient, the quantity corresponding to the extent of compliance of such patient with goals of the therapeutic regimen customized for such patient;
(C) dynamically generating, by the server, from the retrieved data, a patient status listing including, for each patient thereon, an indicator dynamically characterizing, in real time, the quantity corresponding to the extent of compliance of such patient with goals of the therapeutic regimen customized for such patient; and
(D) causing presentation, by the server, over the internet, of the patient status listing on a display of the health practitioner computer system, wherein the patient status listing is configured to enable graphical selection, made on the health practitioner computer system, of a given patient so as to cause display of additional data pertinent to the given patient.

2. A computer-implemented method according to claim 1, further comprising:
causing presentation by the server to the patient via the application running on the mobile computing device, on at least a daily basis, of (iii) a personalized comment reflective of the patient compliance data and configured to provide encouragement to the patient.

3. A computer-implemented method according to claim 1, further comprising:
causing presentation by the server to the patient via the application running on the mobile computing device, on at least a daily basis, of a statistical analysis of performance by the patient that provides at least a quantitative measure of an extent to which the patient has reached a therapeutic goal.

4. A computer-implemented method according to claim 3, further comprising:
causing presentation by the server to the patient via the application running on the mobile computing device, on at least a daily basis, of a statistical analysis of performance by the patient relative to the performance of others.

5. A computer-implemented method according to claim 1, further comprising:
causing presentation by the server to the patient via the application running on the mobile computing device, on at least a daily basis, of a text interface by which the patient can initiate and receive textual communications with a health professional.

6. A computer-implemented method according to claim 1, further comprising:
causing presentation by the server to the patient via the application running on the mobile computing device, on at least a daily basis, of a narrative report of patient activities including interactions with health professionals, specific actions by the patient relative to the regimen, and interactions with individuals in the patient's support network.

7. A computer-implemented method according to claim 1, further comprising:
causing presentation by the server to the patient via the application running on the mobile computing device, on at least a daily basis, of media content selected to assist the patient in achieving goals of the therapeutic regimen.

8. A computer-implemented method according to claim 1, further comprising:
causing presentation by the server to the patient via the application running on the mobile computing device, on at least a daily basis, of media content selected to assist the patient in learning about the medical condition of the patient.

9. A computer-implemented method according to claim 1, further comprising:
receiving at the server from the mobile computing device data, derived from at least one sensor of the mobile computing device, characterizing patient physical activity as recorded by the application running on the mobile computing device, the data selected from the group consisting of location data, GPS data, accelerometer data, pedometer data, heart rate data, photograph data, and video data, and combinations thereof.

10. A computer-implemented method according to claim 1, further comprising:
causing presentation by the server to the patient via the application running on the mobile computing device, on at least a daily basis, of a voice interface by which the patient can initiate and receive voice communications with a health professional.

11. A computer-implemented method according to claim 1, further comprising:
causing presentation by the server to the patient via the application running on the mobile computing device, on at least a daily basis, of a video interface by which the patient can initiate and receive video communications with a health professional.

12. A computer-implemented method according to claim 1, further comprising:
causing presentation by the server to the patient via the application running on the mobile computing device, on at least a daily basis, of a self-assessment interface configured to obtain a self-assessment by the patient and to cause communication of the self-assessment to the server.

13. A computer-implemented method according to claim 1, further comprising:
causing presentation by the server to the patient via the application running on the mobile computing device, on at least a daily basis, of a point score for the patient based on a statistical analysis of activities by the patient demonstrating progress towards goals of the therapeutic regimen, such activities including at least two members of the group consisting of compliance with the regimen, demonstration of understanding of the medical condition, consistency of performance, and interactions with the patient's support network and with other patients.

14. A computer-implemented method according to claim 1, wherein such listing is sorted in reverse order according to extent of compliance.

15. A computer-implemented method according to claim 14, wherein the time-based weighted average of patient tasks completed is based on at least one of (i) a percentage of to-do list items completed in a period of time or (ii) changes in the patient's physiological or pathological values or goals of the therapeutic regime achieved in a period of time.

16. A computer-implemented method according to claim 15, wherein such listing is provided with a patient regimen interface by which the health professional can modify the regimen customized for such patient with a view to improving such patient's progress toward goals of the therapeutic regimen.

17. A computer-implemented method according to claim 1, wherein receiving and storing at the server physiological data pertinent to such patient includes receiving and storing such data from at least one third party application.

18. A computer-implemented method according to claim 1 wherein:
receiving and storing at the server physiological data pertinent to such patient comprises receiving and storing at the server data that characterizes a series of health states defining a natural history of a specific medical condition for such patient, wherein each health state is characterized by a set of physiological and pathological parameter values;
receiving and storing at the server data characterizing a therapeutic regimen for such patient comprises receiving and storing at the server a distinct therapeutic regimen for each health state in the series; and
retrieving and using the physiological data pertinent to a medical condition of such patient to customize the therapeutic regimen for such patient comprises:
storing the physiological and pathological parameter values applicable to the current medical condition of such patient;
processing the physiological and pathological parameter values applicable to the given patient to characterize such patient's current health state; and
processing the current health state of such patient to retrieve the therapeutic regimen for such patient based on such patient's current health state.

19. A computer-implemented method according to claim 18, further comprising:
customizing the retrieved therapeutic regimen based on the specific physiological and pathological parameter values applicable to the current medical condition of such patient.

20. A computer-implemented method according to claim 18, further comprising:
customizing the retrieved therapeutic regimen based on an input provided by a health professional.

21. A computer-implemented method according to claim 1, the method further comprising:
receiving and storing at the server pathological data for patients;
identifying pathological data pertinent to a given patient in a therapeutic regimen for a medical condition of the patient;
using the identified data, identifying a set of other patients having similar pathological data; and
causing transmission, to a mobile computing device of the given patient, of a message introducing a member of the identified set to the given patient.

22. A computer-implemented method according to claim 21, wherein:
receiving and storing pathological data for patients comprises receiving and storing demographic data for patients; and
identifying a set of other patients having similar pathological data comprises identifying demographic data pertinent to the given patient and identifying a set of other patients having similar pathological and demographic data.

23. A computer-implemented method according to claim 21, wherein:
receiving and storing pathological data for patients comprises receiving and storing location data for patients; and
identifying a set of other patients having similar pathological data comprises identifying location data of the given patient and identifying a set of other patients having similar pathological and location data.

24. A computer-implemented method according to claim 23, wherein location data includes at least one of (i) GPS data gathered from mobile computing devices of patients and stored in the server and (ii) residential addresses of patients.

25. A computer-implemented method according to claim 21, wherein:
receiving and storing pathological data for patients comprises receiving and storing regimen compliance data for patients; and identifying a set of other patients having similar pathological data comprises identifying regimen compliance data of the given patient and identifying a set of other patients having similar pathological and regimen compliance data.

* * * * *

UNITED STATES PATENT AND TRADEMARK OFFICE
CERTIFICATE OF CORRECTION

Page 1 of 1

PATENT NO. : 9,805,163 B1
APPLICATION NO. : 14/248854
DATED : October 31, 2017
INVENTOR(S) : Panch et al.

It is certified that error appears in the above-identified patent and that said Letters Patent is hereby corrected as shown below:

In Column 23, Line 52:
Replace "complete"
With --completed--

In Column 25, Line 48:
Replace "regime"
With --regimen--

Signed and Sealed this
Thirty-first Day of July, 2018

Andrei Iancu
*Director of the United States Patent and Trademark Office*